(12) United States Patent
Kahn et al.

(10) Patent No.: US 6,413,963 B2
(45) Date of Patent: *Jul. 2, 2002

(54) REVERSE-TURN MIMETICS AND METHODS RELATING THERETO

(75) Inventors: Michael Kahn, Kirkland; Masakatsu Eguchi, Bellevue; Hwa-Ok Kim, Redmond; Marcin Stasiak, Kirkland, all of WA (US)

(73) Assignee: Molecumetics, Ltd., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/742,682

(22) Filed: Dec. 19, 2000

Related U.S. Application Data

(63) Continuation of application No. 09/344,221, filed on Jun. 25, 1999, now Pat. No. 6,184,223, which is a continuation-in-part of application No. 08/846,432, filed on Apr. 30, 1997, now Pat. No. 6,013,458, which is a continuation-in-part of application No. 08/549,007, filed on Oct. 27, 1995, now Pat. No. 5,929,237.

(51) Int. Cl.$^7$ .................. A61K 31/4985; C07D 487/04; G01N 33/543

(52) U.S. Cl. ...................... 514/249; 544/279; 544/350; 544/91; 540/469; 540/473; 540/552; 540/568; 435/7.1

(58) Field of Search ................. 544/279, 350, 544/91; 540/473, 469, 552, 568; 435/7.1; 514/249, 183

(56) References Cited

U.S. PATENT DOCUMENTS

| | | | |
|---|---|---|---|
| 5,440,013 A | 8/1995 | Kahn | 530/317 |
| 5,545,568 A | 8/1996 | Ellman | 436/518 |
| 5,929,237 A | 7/1999 | Kahn | 544/279 |
| 6,013,458 A | 1/2000 | Kahn et al. | 435/7.1 |
| 6,184,223 B1 | 2/2001 | Kahn et al. | 514/249 |

FOREIGN PATENT DOCUMENTS

| | | |
|---|---|---|
| WO | WO 92/13878 | 8/1992 |
| WO | WO 94/03494 | 2/1994 |
| WO | WO 96/22304 | 7/1996 |
| WO | WO 96/30396 | 10/1996 |
| WO | WO 97/15557 | 5/1997 |
| WO | WO 97/15577 | 5/1997 |
| WO | WO 98/05333 | 2/1998 |
| WO | WO 98/49168 | 11/1998 |

OTHER PUBLICATIONS

Abignente et al., "Research on heterocyclic compounds. XVI. 2–Methylimidazo[1,2–a]pyrazine–3–carboxylic acids," *Chemical Abstracts Database*, Accession No. 103:87841, 1985.

Barrow et al., "Spiroquinazoline, a novel substance P inhibitor with a new carbon skeleton, isolated from *Aspergillus flavipes*,"*Chemical Abstracts Database*, Accession No. 121:129499, 1994.

Cutler et al., "Clinereain: a novel metabolite with plant growth regulating properties from *Botrytis cinerea*," *Chemical Abstracts Database*, Accession No. 109:165645, 1988.

Dennin et al., "Synthesis of derivatives of pyrazino[1,2–a]pyrimidin–4–ones," *Chemical Abstracts Database*, Accession No. 114:164135, 1991.

Faehnle and Rothe, "Syntheses and reactions of peptide cyclols," *Chemical Abstracts Database*, Accession No. 102:7061, 1985.

Gatta et al., "New [f]–fused xanthines: synthesis of 1,3–dipropyl–1H, 3H–pyrazino, pyrido, pyrimido and pyrrolo [2,1–f]purine–2,4–diones," *Chemical Abstracts Database*: 121:57444, 1994.

Kadam et al., "Fermentative manufacture of multiple drup resistance–attenuating ardeemins," *Chemical Abstracts Database*, Accession No. 121:7435, 1994.

Kappe and Kappe, "Cross–conjugated and pseudo–cross–conjugated mesomeric betaines. XVII. Bicyclic mesoionic pyrimidines with cardiovascular activity," *Chemical Abstracts Database*, Accession No. 116:83634, 1992.

Lam et al., *Nature* 354:82–84, 1994.

Lucente et al., "Synthesis and x–ray crystal structure of a tripeptidic cyclol," *Chemical Abstracts Database*, Accession No. 96:69410, 1982.

Numata et al., "Structures of cytotoxic substances and new quinazoline derivatives produced by a fungus form a saltwater fish," *Chemical Abstracts Database*, Accession No. 116:210833, 1992.

Okawara et al., "Preparation and hydrogenolysis of fused piperazines by reaction of diamine and triamine derivatives with benzil. Applications to the synthesis of terminal N–monoprotected triamines," *Chemical Abstracts Database*, Accession No. 117:191810.

Okawara et al., "Simple preparation of terminal N–monoprotected triamines using fused piperazines," *Chemical Abstracts Database*, Accession No. 114:101300, 1991.

Penn et al., "biosynthesis of glyantrypine by *Aspergillus clavatus*," *Chemical Abstracts Database*, Accession No. 117:44249, 1992.

Penn et al., "Glyantrypine, a novel anthranilic acid–containing metabolite of *Aspergillus clavatus*," *Chemical Abstracts Database*, Accession No. 117:127875, 1992.

(List continued on next page.)

*Primary Examiner*—Charanjit S. Aulakh
(74) *Attorney, Agent, or Firm*—Seed IP Law Group PLLC

(57) ABSTRACT

Conformationally constrained compounds which mimic the secondary structure of reverse-turn regions of biologically active peptides and proteins are disclosed. Such reverse-turn mimetics have utility in the treatment of cell adhesion-indicated diseases, such as multiple sclerosis, atherosclerosis, asthma and inflammatory bowel disease.

19 Claims, 9 Drawing Sheets

OTHER PUBLICATIONS

Pinnen et al., "Cyclization under mild conditions of anthraniloyl and N–methylanthraniloyl dipeptides," *Chemical Abstracts Database*, Accession No. 110:76029, 1989.

Pinnen et al., "Ten–membered cyclotripeptides: influence of the ring–flexibility on intramolecular reactions," *Chemical Abstracts Database*, Accession No.102:132448, 1985.

Rothe et al., "Cyclol formation during tripeptide cyclizations. Synthesis of a secondary cyclotripeptide, cyclo-(D–Phe–L–Pro–L–Pro)," *Chemical Abstracts Database*, Accession No. 97:56231, 1982.

Rothe et al., "Secondary all–L–cyclotripeptides," *Chemical Abstracts Database*, Accession No. 103:215766, 1985.

Sauter et al., "Novel basically substituted pyrimidines and benzothienopyrimidines," *Chemical Abstracts Database*, Accession No. 87:84931, 1977.

Tanaka and Narita, "Syntheses of pyrido[2,3–b]pyrazine derivatives," *Chemical Abstracts Database*, Accession No. 84:31002, 1975.

Jackson et al., "Potent $\alpha 4\beta 1$ Peptide Antagonists as Potential Anti–Inflammatory Agents," *J. of Medical Chemistry* *40*(21): 3359–3368, 1997.

Ku et al., "Direct Design of a Potent Non–Peptide Fibrinogen Receptor Antagonist Based on the Structure and Conformation of a Highly Constrained Cyclic RGD Peptide," *J. of American Chemical Society 115*(19): 8861–8862, 1993.

Souers et al., "Novel Inhibitors of $\alpha 4\beta 1$ Integrin Receptor Interactions through Library Synthesis and Screening," *Bioorganic & Medicinal Chemistry Letters 8*: 2297–2302, 1998.

REVERSE-TURN MIMETICS AND METHODS RELATING THERETO

CROSS-REFERENCE TO RELATED APPLICATION

This application is a continuation of U.S. application Ser. No. 09/344,221 filed Jun. 25, 1999 now U.S. Pat. No. 6,184,223, which is a continuation-in-part of U.S. application Ser. No. 08/846,432, filed Apr. 30, 1997 now U.S. Pat. No. 6,013,458, which is a continuation in part of U.S. application Ser. No. 08/549,007, filed Oct. 27, 1995 now U.S. Pat. No. 5,929,237.

TECHNICAL FIELD

The present invention relates generally to reverse-turn mimetics, including inhibitors of cell adhesion-mediated disease, as well as to a chemical library of reverse-turn mimetics.

BACKGROUND OF THE INVENTION

Cell adhesion is critical to the viability of living organisms. Adhesion holds multicellular tissues together and directs embryonic development. It plays important roles in wound healing, eradication of infection and blood coagulation. Integrins are a family of cell surface proteins intimately involved in all of these functions. They have been found in nearly every type of human cell except red blood cells. Abnormalities in integrin function contribute to a variety of disorders including inflammatory diseases, heart attack, stroke, and cancer.

Integrins consist of heterodimers of $\alpha$ and $\beta$ subunits, non-covalently bound to each other. These cell surface receptors extend through the cell membrane into the cytoplasm. At least 15 different $\alpha$ and 9 different $\beta$ subunits are known. However, because most $\alpha$ proteins associate with only a single $\beta$ there are about 21 known integrin receptors. On the cell surface the heads of the two subunits contact each other to form a binding surface for extracellular protein ligands, allowing attachment to other cells or to the extracellular matrix. The affinity of these receptors may be regulated by signals from outside or within the cell. For example, recruitment of leukocytes to the site of injury or infection involves a series of adhesive interactions. Weak interaction between endothelial and leukocyte selectins and carbohydrates mediate transient adhesion and rolling of the leukocyte along the vessel wall. Various chemokines and other trigger factors released by the site of inflammation serve as signals to activate integrins from a quiescent to a high affinity state. These activated integrins then bind their cognate ligands on the surface of the endothelial cells, resulting in strong adhesion and flattening of the leukocyte. Subsequently the leukocyte migrates through the endothelium into the tissue below.

Integrin $\alpha_4\beta_1$ mediates cell adhesion primarily through binding to either vascular cell adhesion molecule-1 (VCAM-1) or an alternatively spliced variant of fibronectin containing the type III connecting segment (IIICS). A variety of cells involved in inflammation express $\alpha_4\beta_1$, including lymphocytes, monocytes, basophils and eosinophils, but not neutrophils. Monoclonal antibodies to the $\alpha_4$ subunit have been used to validate $\alpha_4$-containing integrins as potential therapeutic targets in animal models of rheumatoid arthritis (Barbadillo et al. *Springer Semin Immunopathol* 16: 427–36, 1995; Issekutz et al. *Immunology* 88: 569–76, 1996), acute colitis (Podolsky et al. *J Clin Invest* 92: 372–80, 1993), multiple sclerosis (Yednock et al. *Nature* 356: 63–6, 1992), asthma (Abraham et al. *J. Clin. Invest.* 93: 776–87, 1994; U.S. Pat. No. 5,871,734) and diabetes (Tsukamoto et al. *Cell Immunol* 165: 193–201, 1995). More recently, low molecular weight peptidyl derivatives have been produced as competitive inhibitors of $\alpha_4\beta_1$ and one has been shown to inhibit allergic airway responses in sheep (Lin et al. *J Med Chem* 42: 920–34, 1999).

It has been shown that a key sequence in IIICS involved in binding to $\alpha_4\beta_1$ is the 25 residue peptide CS1, and within that sequence the minimally recognized motif is the tripeptide, LDV. A similar sequence, IDS, has been implicated in the binding of VCAM-1 to $\alpha_4\beta_1$. X-ray crystal structures of an N-terminal two-domain fragment of VCAM-1 show that the IDS sequence is part of an exposed loop linking two beta-strands (Jones et al. *Nature* 373: 539–44, 1995; Wang et al. *Proc Natl Acad Sci U S A* 92: 5714–8, 1995). Cyclic peptides and derivatives thereof which adopt reverse-turn conformations have proven to be inhibitors of VCAM-1 binding to $\alpha_4\beta_1$ (WO 96/00581; WO 96/06108; Doyle et al. *Int J Pept Protein Res* 47: 427–36, 1996). In addition, a number of potent and selective (versus $\alpha_5\beta_1$) cyclic peptide-based inhibitors have been discovered (Jackson et al. *J Med Chem* 40: 3359–68, 1997). Several non-peptidyl beta-turn mimetics have also been reported to bind $\alpha_4\beta_1$ with $IC_{50}$s in the low micromolar range (Souers et al. *Bioorg Med Chem Lett* 8: 2297–302, 1998). Numerous phenylalanine and tyrosine derivatives have also been disclosed as inhibitors of $\alpha_4\beta_1$ (WO 99/06390; WO 99/06431; WO 99/06433; WO 99/06434; WO 99/06435; WO 99/06436; WO 99/06437; WO 98/54207; WO 99/10312; WO 99/10313; WO 98/53814; WO 98/53817; WO 98/58902) However, no potent and orally available small molecule inhibitors have been disclosed.

A related integrin, $\alpha_4\beta_7$, is expressed on the surface of lymphocytes and binds VCAM-1, fibronectin and mucosal addressin cell adhesion molecule 1 (MAdCAM-1). Integrin $\alpha_4\beta_7$ and MAdCAM mediate recirculation of a subset of lymphocytes between the blood, gut, and lymphoid tissue. Similar to VCAM-1 and Fibronectin CS-1 there is a tripeptide sequence, LDT, present on the CD loop of MAdCAM-1 which is important for recognition by $\alpha_4\beta_7$. An X-ray crystal structure shows this sequence is also part of a turn structure (Tan et al. *Structure* 6: 793–801, 1998). Recent studies have shown that $\alpha_4\beta_7$ may also play a part in diseases such as asthma (Lobb et al. *Ann N Y Acad Sci* 796: 113–23, 1996), inflammatory bowel disease (Fong et al. *Immunol Res* 16: 299–311, 1997), and diabetes (Yang et al. *Diabetes* 46: 1542–7, 1997). In addition, while $\alpha_4$ integrins appear to be down-regulated in carcinomas such as cervical and prostate, they appear to be up-regulated in metastatic melanoma (Sanders et al. *Cancer Invest* 16: 329–44, 1998), suggesting that inhibitors of $\alpha_4\beta_1$ and $\alpha_4\beta_7$ may be useful as anticancer agents.

Reverse-turns comprise one of three classes of protein secondary structure and display three (gamma-turn), four (beta-turns), or more (loops) amino acid side chains in a fixed spatial relationship to each other. Turns have proven important in molecular recognition events (Rose et al. *Advances in Protein Chemistry* 37: 1–109, 1985) and have engendered a burgeoning field of research into small molecule mimetics of them (e.g. Hanessian et al. *Tetrahedron* 53: 12789–12854, 1997). Many mimetics have either been external turn-mimetics which do not allow for the display of all the physiologically relevant side-chains (e.g. Freidinger et al. *Science* 210: 656–8, 1980) or small, conformationally mobile cyclic peptide derivatives (e.g. Viles et al. *Eur J*

Biochem 242: 352–62, 1996). However, non-peptide compounds have been developed which closely mimic the secondary structure of reverse-turns found in biologically active proteins or peptides. For example, U.S. Pat. Nos. 5,475,085, 5,670,155 and 5,672,681, to Kahn and published PCT WO94/03494 to Kahn all disclose conformationally constrained, non-peptidic compounds which mimic the three-dimensional structure of reverse-turns. More recently, published PCT WO97/15577 to Kahn and PCT WO98/49168 to Kahn et al. have disclosed additional, highly constrained bicyclic heterocycles as reverse-turn mimetics. Nevertheless, as no one template can mimic every type of turn, there remains a need in the art for additional reverse-turn templates and methods for their use.

While significant advances have been made in the synthesis and identification of conformationally constrained, reverse-turn mimetics, there is still a need in the art for small molecules that mimic the secondary structure of peptides. In addition, there is a need in the art for techniques for synthesizing libraries of such mimetics and screening the library members against biological targets to identify bioactive library members. Further, there is a need in the art for small, orally available inhibitors of integrins, for use in treating inflammatory diseases and cardiovascular diseases, as well as some cancers. In particular there is a need for inhibitors of $\alpha_4\beta_1$ and $\alpha_4\beta_7$, for use in the treatment of rheumatoid arthritis, asthma, diabetes and inflammatory bowel disease. The present invention fulfills these needs, and provides further related advantages.

SUMMARY OF THE INVENTION

In brief, the present invention is directed to conformationally constrained compounds which mimic the secondary structure of reverse-turn regions of biologically active peptides and proteins. This invention also discloses libraries containing such compounds, as well as the synthesis and screening thereof. Furthermore, the invention discloses the use of reverse-turn mimetics for the treatment of cell adhesion-mediated diseases.

The compounds of the present invention have the following general structure (I):

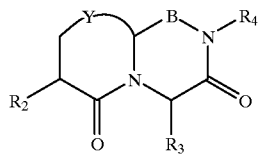

wherein Y is selected from —CH($R_5$)-A-N($R_1$)—, -A-N($R_1$)—CH(R')—, -A-N($R_1$)—C(=O)—, -A-C(=O)—N($R_1$)—, -A-CH($R_1$)—O—, and -A-CH($R_1$)—N(R')—; A is —(CHR')$_n$—; B is —(CHR'')$_m$—; n=0, 1 or 2; m=1, 2 or 3; and any two adjacent CH groups or adjacent NH and CH groups on the bicyclic ring may optionally form a double bond; and wherein R', R'', $R_1$, $R_2$, $R_3$, $R_4$ and $R_5$ are as defined in the following detailed description.

In the embodiment wherein Y is —CH($R_5$)-A-N($R_1$)—, the compounds of this invention have the following structure (I'):

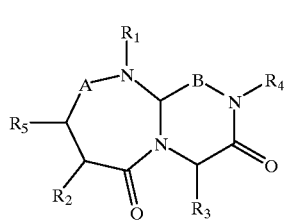

wherein A and B are as defined above, and $R_1$, $R_2$, $R_3$, $R_4$ and $R_5$ are as defined in the following detailed description.

In the embodiment wherein Y is -A-N($R_1$)—CH(R')—, the compounds of this invention have the following structure (I''):

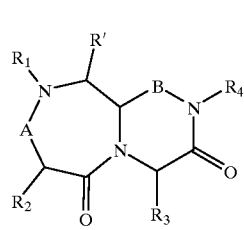

wherein A and B are as defined above, and R', $R_1$, $R_2$, $R_3$ and $R_4$ are as defined in the following detailed description.

In the embodiment wherein Y is -A-N($R_1$)—C(=O)—, the compounds of this invention have the following structure (I'''):

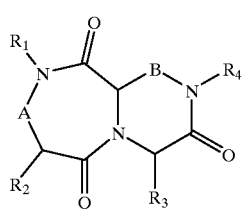

wherein A and B are as defined above, and $R_1$, $R_2$, $R_3$ and $R_4$ are as defined in the following detailed description.

In the embodiment wherein Y is -A-C(=O)—N($R_1$)—, the compounds of this invention have the following structure (I''''):

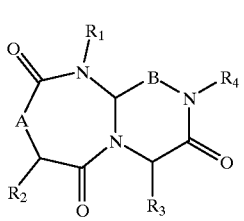

wherein A and B are as defined above, and $R_1$, $R_2$, $R_3$ and $R_4$ are as defined in the following detailed description.

In the embodiment wherein Y is -A-CH($R_1$)—O—, the compounds of this invention have the following structure (I'''''):

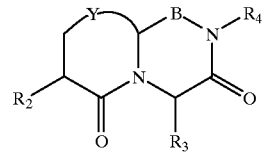

(I)

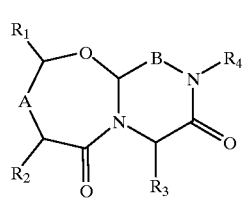

(I'''''')

wherein A and B are as defined above, and $R_1$, $R_2$, $R_3$ and $R_4$ are as defined in the following detailed description.

In the embodiment wherein Y is -A-CH($R_1$)—N(R')—, the compounds of this invention have the following structure (I'''''''):

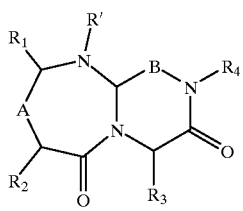

(I''''''')

wherein A and B are as defined above, and R', $R_1$, $R_2$, $R_3$ and $R_4$ are as defined in the following detailed description.

The present invention is also directed to libraries containing compounds of structure (I) above, as well as methods for synthesizing such libraries and methods for screening the same to identify biologically active compounds. Methods of use for treating cell-adhesion-mediated disease with the compounds of this invention are described. Compositions containing a compound of this invention in combination with a pharmaceutically acceptable carrier or diluent are also disclosed.

These and other aspects of this invention will be apparent upon reference to the attached figures and following detailed description. To this end, various references are set forth herein which describe in more detail certain procedures, compounds and/or compositions, and are incorporated by reference in their entirety.

DETAILED DESCRIPTION OF THE INVENTION

Figure 1:
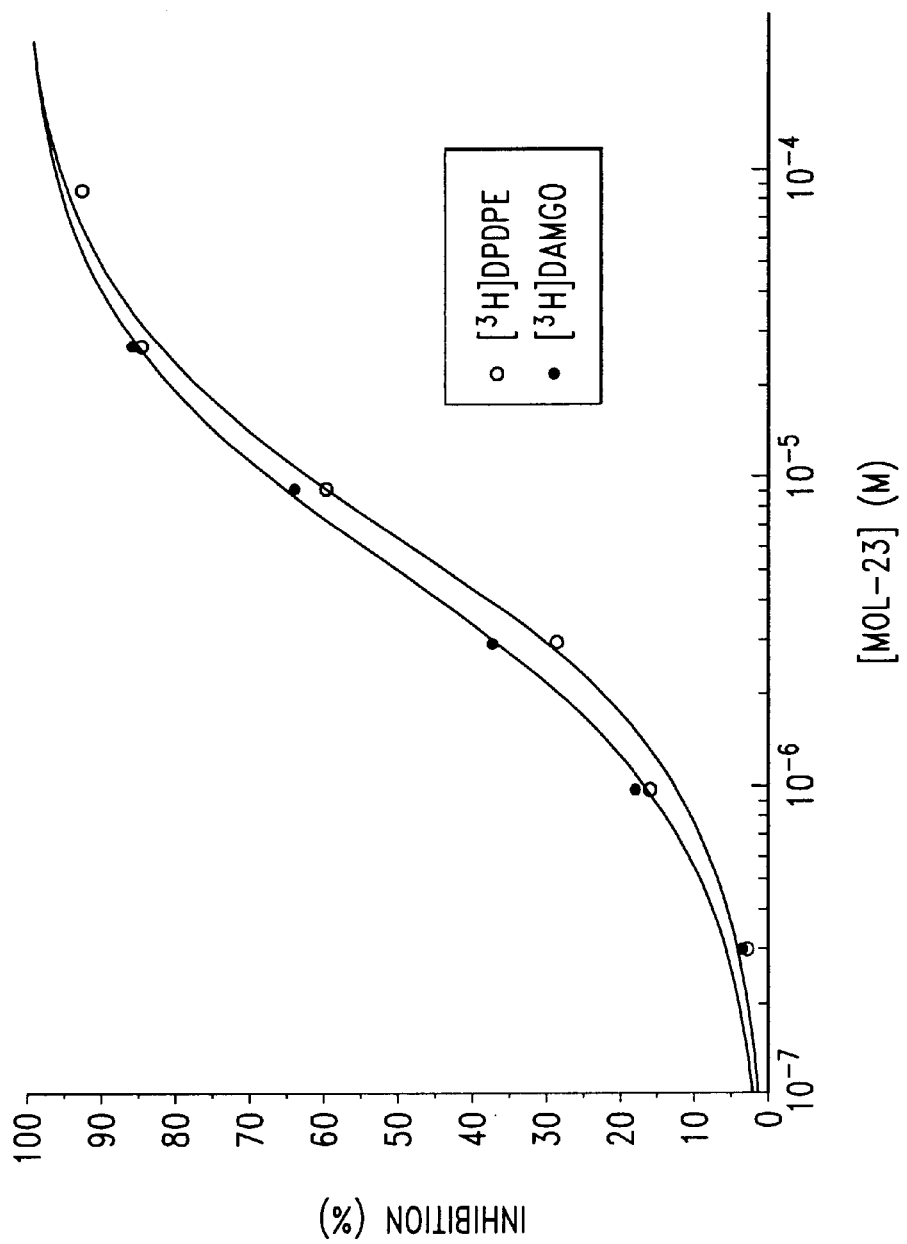
FIG. 1 illustrates the percent inhibition of radioligand binding to δ and μ opiate receptors of a representative reverse-turn mimetic of this invention as a function of concentration.

The present invention is directed to reverse-turn mimetics and chemical libraries containing reverse-turn mimetics. The reverse-turn mimetics of the present invention are useful as bioactive agents, including (but not limited to) use as diagnostic, prophylactic and/or therapeutic agents. The reverse-turn mimetic libraries of this invention are useful in the identification of such bioactive agents. In the practice of the present invention, the libraries may contain from tens to hundreds to thousands (or greater) of individual reverse-turn mimetics (also referred to herein as "members").

In one aspect of the present invention, a reverse-turn mimetic is disclosed having the following structure (I):

wherein Y is selected from —CH($R_5$)-A-N($R_1$)—, -A-N($R_1$)—CH(R')—, -A-N($R_1$)—C(=O)—, -A-C(=O)—N($R_1$)—, -A-CH($R_1$)—O— and -A-CH($R_1$)—N(R')—; A is —(CHR')—; B is —(CHR")$_m$—; n=0, 1 or 2; m=1, 2 or 3; and any two adjacent CH groups or adjacent NH and CH groups on the bicyclic ring may optionally form a double bond; and wherein R', R", $R_1$, $R_2$, $R_3$, $R_4$ and $R_5$ are as defined below.

In structures (I') through (I''''''') above a solid line designation for attachment of the various R groups to a carbon atom on the fused bicyclic ring indicates that these R groups may lie either above or below the plane of the page. If a reverse-turn mimetic of this invention is intended to mimic a reverse-turn of naturally occurring amino acids (i.e., "L-amino acids"), the R groups would generally lie below the plane of the page (i.e., "⋯⋯ R") in Structure (I). However, if the reverse-turn mimetic of this invention is intended to mimic a reverse-turn containing one or more D-amino acids, then the corresponding R group or groups would lie above the plane of the page (i.e., "◂ R") in Structure (I).

In one embodiment, $R_1$ and $R_4$ are the same or different and represent the remainder of the compound, and R', R", $R_2$, $R_3$, and $R_5$ are the same or different and independently selected from an amino acid side chain moiety or derivative thereof. With regard to R' and R", it should be understood that each occurrence of R' and R" is independently selected from amino acid side chain moieties or derivatives thereof. For example, when m=2, B is a —CHR"CHR"— moiety. In this instance, both occurrences of R" are independently selected, and may be the same or different. Thus, if the first occurrence of R" is hydrogen and the second methyl, B would have the structure —CH$_2$CH(CH$_3$)—.

As used herein, the term "remainder of the compound" means any moiety, agent, compound, support, molecule, linker, amino acid, peptide or protein covalently attached to the reverse-turn mimetic at either the $R_1$ and/or $R_4$ positions. This term also includes amino acid side chain moieties and derivatives thereof.

As used herein, the term "amino acid side chain moiety" represents any amino acid side chain moiety present in naturally occurring proteins including (but not limited to) the naturally occurring amino acid side chain moieties identified in Table 1. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine.

TABLE 1

Amino Acid Side Chain Moieties

| Amino Acid Side Chain Moiety | Amino Acid |
|---|---|
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3$$^+$ | Lysine |
| —(CH$_2$)$_3$NHC(NH$_2$)NH$_2$$^+$ | Arginine |
| —CH$_2$-(imidazole) | Histidine |
| —CH$_2$COO$^-$ | Aspartic acid |
| —CH$_2$CH$_2$COO$^-$ | Glutamic acid |
| —CH$_2$CONH$_2$ | Asparagine |
| —CH$_2$CH$_2$CONH$_2$ | Glutamine |
| —CH$_2$-(phenyl) | Phenylalanine |
| —CH$_2$-(phenyl)-OH | Tyrosine |
| —CH$_2$-(indole) | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| —HN-(pyrrolidine) | Proline |
| —HN-(hydroxypyrrolidine)-OH | Hydroxyproline |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and phenylalanine may generally be classified as lower chain alkyl, aryl, or aralkyl moieties. Derivatives of amino acid side chain moieties include other straight chain or branched, cyclic or noncyclic, substituted or unsubstituted, saturated or unsaturated lower chain alkyl, aryl or aralkyl moieties.

As used herein, "lower chain alkyl moieties" contain from 1–12 carbon atoms, "lower chain aryl moieties" contain from 6–12 carbon atoms and "lower chain aralkyl moieties" contain from 7–12 carbon atoms. Thus, in one embodiment, the amino acid side chain derivative is selected from a C$_{1-12}$ alkyl, a C$_{6-12}$ aryl and a C$_{7-12}$ aralkyl, and in a more preferred embodiment, from a C$_{1-7}$ alkyl, a C$_{6-10}$ aryl and a C$_{7-11}$ aralkyl.

Amino side chain derivatives of this invention further include substituted derivatives of lower chain alkyl, aryl, and aralkyl moieties, wherein the substituent is selected from (but are not limited to) one or more of the following chemical moieties: —OH, —OR, —COOH, —COOR, —CONH$_2$, —NH$_2$, —NHR, —NRR, —SH, —SR, —SO$_2$R, —SO$_2$H, —SOR and halogen (including F, Cl, Br and I), wherein each occurrence of R is independently selected from straight chain or branched, cyclic or noncyclic, substituted or unsubstituted, saturated or unsaturated lower chain alkyl, aryl and aralkyl moieties. Moreover, cyclic lower chain alkyl, aryl and aralkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

Representative R$_1$ and R$_4$ moieties specifically include (but are not limited to) —OH, —OR, —COR, —COOR, —CON$_2$, —CONR, —CONRR, —NH$_2$, —NHR, —NRR, —SO$_2$R and —COSR, wherein each occurrence of R is as defined above.

In a further embodiment, and in addition to being an amino acid side chain moiety or derivative thereof (or the remainder of the compound in the case of R$_1$ and R$_4$), R$_1$, R$_2$, R$_3$, R$_4$, or R$_5$ may be a linker facilitating the linkage of the compound to another moiety or compound. For example, the compounds of this invention may be linked to one or more known compounds, such as biotin, for use in diagnostic or screening assay. Furthermore, R$_1$, R$_2$, R$_3$, R$_4$ or R$_5$ may be a linker joining the compound to a solid support (such as a support used in solid phase peptide synthesis) or alternatively, may be the support itself. In this embodiment, linkage to another moiety or compound, or to a solid support, is preferable at the R$_1$ or R$_4$ position, and more preferably at the R$_4$ position.

In the embodiment where Y is —CH(R$_5$)-A-N(R$_1$)—, the reverse-turn mimetic has the following structure (I'):

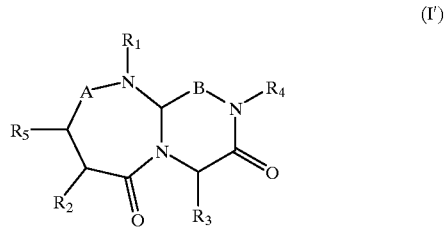

(I')

wherein A, B, R$_1$, R$_2$, R$_3$, R$_4$ and R$_5$ are as defined above. In a preferred embodiment, R$_1$ and R$_4$ represent the remainder of the compound, and R$_2$, R$_3$ and R$_5$ are individually selected from an amino acid side chain moiety.

In a more specific embodiment of structure (I'), A is —(CH$_2$)$_n$—, B is —(CH$_2$)$_m$—, and the reverse-turn mimetic has the following structure (Ia'):

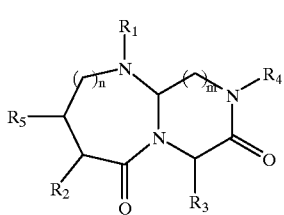
(Ia')

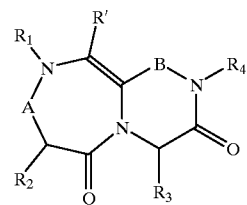
(Ia")

wherein n, m, $R_1$, $R_2$, $R_3$, $R_4$ and $R_5$ are as defined above. In a preferred embodiment, $R_1$ and $R_4$ represent the remainder of the compound, and $R_2$, $R_3$ and $R_5$ are individually selected from an amino acid side chain moiety.

In a yet more specific embodiment of structure (I'), A is $—(CH_2)_n—$, B is $—(CH_2)_m—$, n is 0, m is 1 and the reverse-turn mimetic has the following structure (Ib'):

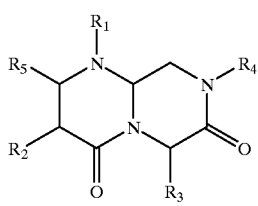
(Ib')

wherein $R_1$, $R_2$, $R_3$, $R_4$ and $R_5$ are as defined above. In a preferred embodiment, $R_1$ and $R_4$ represent the remainder of the compound, and $R_2$, $R_3$ and $R_5$ are individually selected from an amino acid side chain moiety. In another preferred embodiment, $R_1$ is selected from ROC(O)—, $RSO_2$— and RNHC(O)—, wherein R is as defined above. In a more preferred embodiment, $R_1$ is selected from ROC(O)—, $RSO_2$— and RNHC(O)— and R is selected from substituted or unsubstituted lower chain aryl and lower chain aralkyl moieties. In another specific embodiment, $R_2$ and $R_5$ are independently selected from lower chain alkyl moieties, substituted with COOH or COOR, wherein R is as defined above. In another specific embodiment, $R_3$ is selected from substituted or unsubstituted lower chain aryl and lower chain aralkyl moieties.

In the embodiment where Y is -A-N($R_1$)—CH(R')—, the reverse-turn mimetic has the following structure (I").

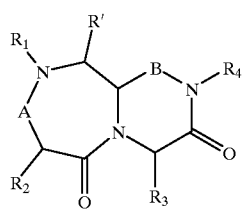
(I")

wherein A, B, $R_1$, $R_2$, $R_3$, $R_4$ and R' are as defined above. In a preferred embodiment, $R_1$ and $R_4$ represent the remainder of the compound, and $R_2$, $R_3$ and R' are individually selected from an amino acid side chain moiety.

In an embodiment of structure (I") where two adjacent CH groups on the bicyclic ring form a double bond, the reverse-turn mimetics of this invention include the following structure (Ia"):

wherein A, B, $R_1$, $R_2$, $R_3$, $R_4$ and R' are as defined above. In a preferred embodiment, $R_1$ and $R_4$ represent the remainder of the compound, $R_2$ and $R_3$ are independently selected from an amino acid side chain moiety, and R' is hydrogen.

In a more specific embodiment of structure (Ia"), A is $—(CH_2)_n—$, B is $—(CH_2)_m—$, R' is hydrogen, and the reverse-turn mimetic has the following structure (Ib"):

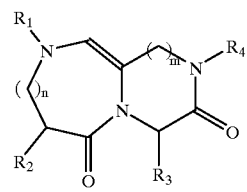
(Ib")

wherein n, m, $R_1$, $R_2$, $R_3$ and $R_4$ are as defined above.

In the embodiment where Y is -A-N($R_1$)—C(=O)—, the reverse turn mimetic has the following structure (I'''):

(I''')

wherehin A, B, $R_1$, $R_2$, $R_3$ and $R_4$ are as defined above. In a preferred embodiment, $R_1$ and $R_4$ represent the remainder of the compound, and $R_2$ and $R_3$ are independently selected from an amino acid side chain moiety.

In a more specific embodiment of structure (I'''), A is $—(CH_2)_n—$, B is $—(CH_2)_m—$, and the reverse-turn mimetic has the following structure (Ia'''):

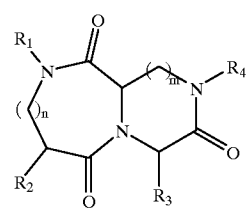
(Ia''')

wherein n, m, $R_1$, $R_2$, $R_3$ and $R_4$ are as defined above.

In the embodiment where Y is -A-C(=O)—N($R_1$)—, the reverse turn mimetic has the following structure (I''''):

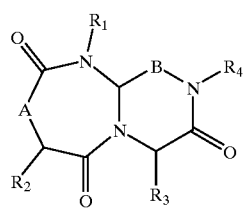
(I''')

wherein $R_1$, $R_2$, $R_3$ and $R_4$ are as defined above. In a preferred embodiment, $R_1$ and $R_4$ represent the remainder of the compound, and $R_2$ and $R_3$ are independently selected from an amino acid side chain moiety.

In a more specific embodiment of structure (I'''), A is —$(CH_2)_n$—, B is —$(CH_2)_m$—, and the reverse-turn mimetic has the following structure (Ia''''):

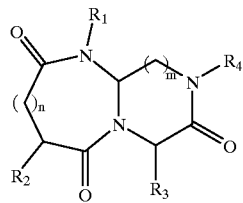
(Ia'''')

wherein n, m, $R_1$, $R_2$, $R_3$ and $R_4$ are as defined above.

In the embodiment where Y is -A-CH($R_1$)—O—, the reverse-turn mimetic has the following structure (I''''):

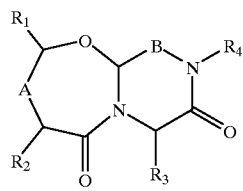
(I''''')

wherein $R_1$, $R_2$, $R_3$ and $R_4$ are as defined above. In a preferred embodiment, $R_1$ and $R_4$ represent the remainder of the compound, and $R_2$ and $R_3$ are independently selected from an amino acid side chain moiety.

In a more specific embodiment of structure (I''''), A is —$(CH_2)_n$—, B is —$(CH_2)_m$—, and the reverse-turn mimetic has the following structure (Ia''''):

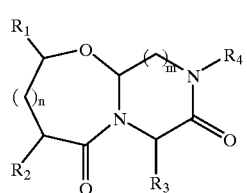
(Ia''''')

wherein n, m, $R_1$, $R_2$, $R_3$ and $R_4$ are as defined above.

In the embodiment where Y is -A-CH($R_1$)—N(R')—, and adjacent NH and CH groups on the bicyclic ring form a double bond, the reverse-turn mimetics of this invention include the following structure (Ia'''''):

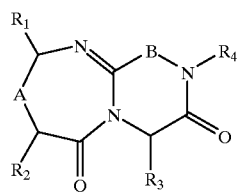
(Ia''''')

wherein A, B, $R_1$, $R_2$, $R_3$ and $R_4$ are as defined above. In a preferred embodiment, $R_1$ and $R_4$ represent the remainder of the compound, and $R_2$ and $R_3$ are independently selected from an amino acid side chain moiety.

In a more specific embodiment of structure (Ia'''''), A is —$(CH_2)_n$—, B is —$(CH_2)_m$—, and the reverse-turn mimetic has the following structure (Ib''''):

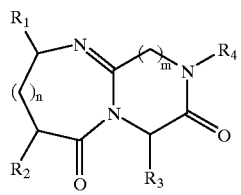
(Ib''''')

wherein n, m, $R_1$, $R_2$, $R_3$ and $R_4$ are as defined above.

In preferred embodiment of structure (I), $R_1$ is selected from ROC(o)-, $RSO_2$— AND RHNC(O)—, wherein R is as defined above. In a more specific embodiment, $R_1$ is selected from ROC(O)—, $RSO_2$— and RHNC(O) and R is selected from substituted or unsubstituted lower chain aryl and lower chain aralykl moieties.

In a specific embodiment of structure (I), $R_2$ and $R_5$ are independently selected from lower chain alkyl moieties, substituted with COOH or COOR, wherein R is as defined above. In another specific embodiment of structure (I), $R_2$ and $R_5$ are independently selected from H— and RC(O)NH— wherein R is as defined above.

In another specific embodiment of structure (I), $R_3$ is selected from substituted or unsubstituted lower chain aryl and lower chain aralkyl moieties.

In another specific embodiment of structure (I), $R_3$ is selected from substituted or unsubstituted lower chain aryl and lower chain aralkyl, including hererocyclic, moieties.

The reverse-turn mimetics of the present invention may be prepared by utilizing appropriate starting component molecules (hereinafter referred to as "component pieces"). Briefly, in the synthesis of reverse turn mimetics having structure (I'), first and second component pieces are coupled to form a combined first-second intermediate, third and fourth component pieces are coupled to form a combined third-fourth intermediate (or, if commercially available, a single third intermediate may be used), the combined first-second intermediate and third-fourth intermediate (or third intermediate) are then coupled to provide a first-second-third-fourth intermediate (or first-second-third intermediate) which is cyclized to yield the reverse-turn mimetics of this invention. Alternatively, the reverse-turn mimetics of structure (I') may be prepared by sequential coupling of the individual component pieces either stepwise in solution or by solid phase synthesis as commonly practiced in solid phase peptide synthesis.

Within the context of the present invention, a "first component piece" has the following structure 1:

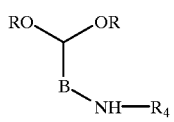

1 where $R_4$ and B are as defined above, and R is a protective group suitable for use in peptide synthesis. Suitable R groups include alkyl groups and, in a preferred embodiment, R is a methyl group. Such first component pieces may be readily synthesized by reductive amination by mating $CH(OR)_2$—$(CH_2)m$-CHO with $H_2N$—$R_4$, or by displacement from $CH(OR)_2$—$(CH_2)m$-Br. Alternatively, one of the R-groups may be a linker and resin. Polystyrene resins, such as those typically used in peptide synthesis and containing the Wang linker (4-hydroxymethylphenoxybutyrate), are suitable.

A "second component piece" of this invention has the following structure 2:

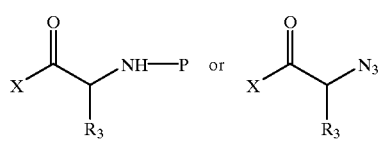

2 where $R_3$ is as defined above, P is an amino protective group suitable for use in peptide synthesis, and X represents the leaving group of the activated carboxylic acid group. Preferred protective groups include t-butyl dimethylsilyl (TBDMS), BOC, FMOC, and Alloc (allyloxycarbonyl). N-Protected amino acids are commercially available. For example, FMOC amino acids are available from a variety of sources. The conversion of these compounds to the second component pieces of this invention may be readily achieved by activation of the carboxylic acid group of the N-protected amino acid. Suitable activated carboxylic acid groups include acid halides where X is a halide such as chloride or bromide, acid anhydrides where X is an acyl group such as acetyl, reactive esters such as an N-hydroxybenzotriazole esters, N-hydroxysuccinimide esters and pentafluorophenyl esters, and other activated intermediates such as the active intermediate formed in a coupling reaction using a carbodiimide such as dicyclohexylcarbodiimide (DCC) or diisopropylcarbodiimide (DIC).

In the case of the azido derivative of an amino acid serving as the second component piece, such compounds may be prepared from the corresponding amino acid by the reaction disclosed by Zaloom et al. (*J. Org. Chem.* 46:5173–76, 1981).

A "third component piece" of this invention has the following structure 3:

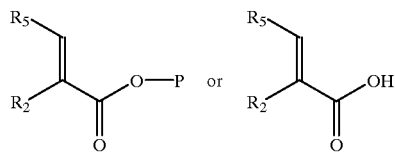

3 where $R_2$ and $R_5$ are as defined above, and P is a carboxylic acid protective group such as a methyl or t-butyl group.

A "fourth component piece" of this invention has the following structure 4:

$R_1$—$NH_2$

4 where $R_1$ is as defined above. Suitable fourth component pieces are commercially available from a variety of sources. Alternatively, the fourth component pieces may be readily prepared by standard organic synthetic techniques commonly utilized for the synthesis of primary amines.

More specifically, the reverse-turn mimetics of this invention of structure (I') are synthesized by reacting a first component piece with a second component piece to yield a combined first-second intermediate, followed by either reacting the combined first-second intermediate with third and fourth component pieces sequentially, or reacting the intermediate with a combined third-fourth intermediate to provide a combined first-second-third-fourth intermediate, and then cyclizing this intermediate to yield the reverse-turn mimetic.

The general synthesis of a reverse-turn mimetic having structure I' may be synthesized by the following technique. A first component piece 1 is coupled to a second component piece 2 to yield, after N-deprotection, a combined first-second intermediate 1-2 as illustrated below:

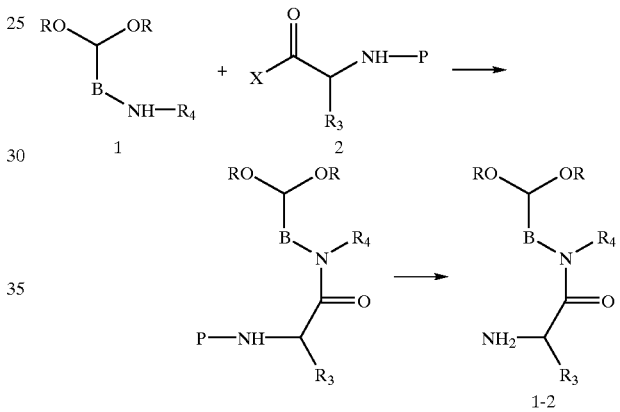

The synthesis of the reverse-turn mimetic may be convergent, in which case a combined third-fourth intermediate 3-4 is prepared from the coupling of a third component piece 3 with a fourth component piece 4 to yield, after O-deprotection, a combined third-fourth intermediate 3-4 as illustrated below:

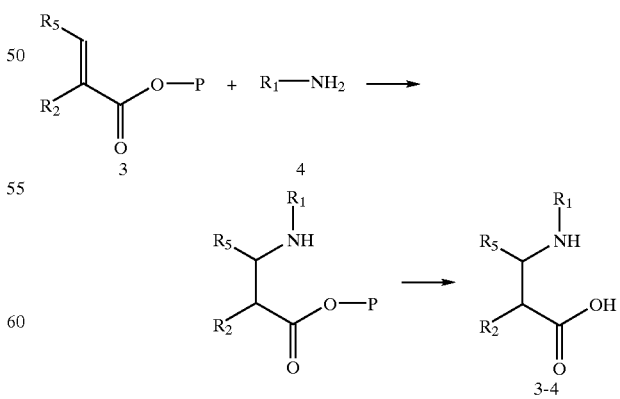

In the case where n of structure (I) above is 1 or 2, an intermediate of the following structure 3-4' can be made as follows:

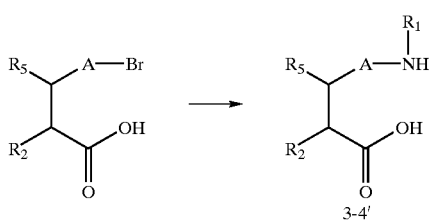

3-4' wherein A is —(CHR')$_n$—. Intermediate 3-4' may then be employed in place of intermediate 3-4 in the following reactions to yield a reverse-turn mimetic of this invention having structure (I'). Alternatively, in the case where n of structure (I) above is 1, 2 or 3, 3-4' may be made from a beta-, gamma- or delta-amino acid derivative which is acylated or sulfonylated and then O-deprotected as follows:

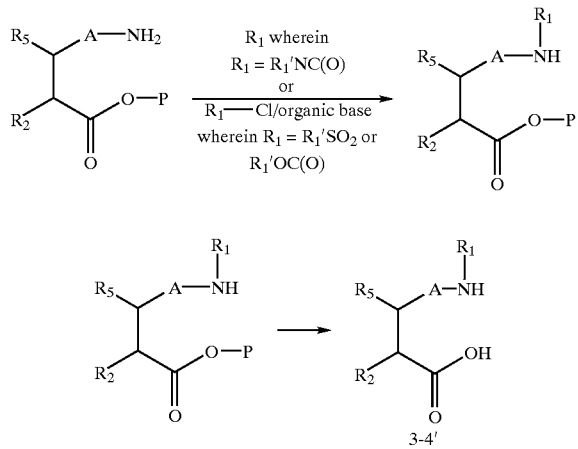

3-4'

Coupling of the combined intermediates 1-2 and 3-4 provides intermediate 1-2-3-4 which, upon cyclization, yield the reverse-turn mimetic (I') as illustrated below:

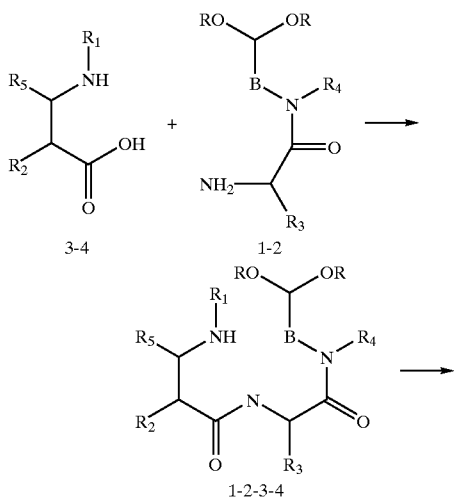

1-2-3-4

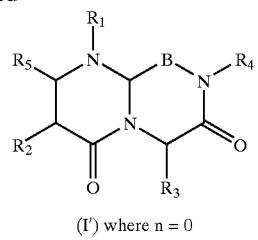

(I') where n = 0

The syntheses of representative component pieces of this invention are described in Example 1. The syntheses of representative combined first-second and third-fourth intermediates are described in Examples 2 and 3, respectively. The coupling of these intermediates to form a representative combined first-second-third-fourth intermediate is described in Example 4. The cyclization of this intermediate to form a representative reverse-turn mimetic is described in Example 5.

Figure 2:
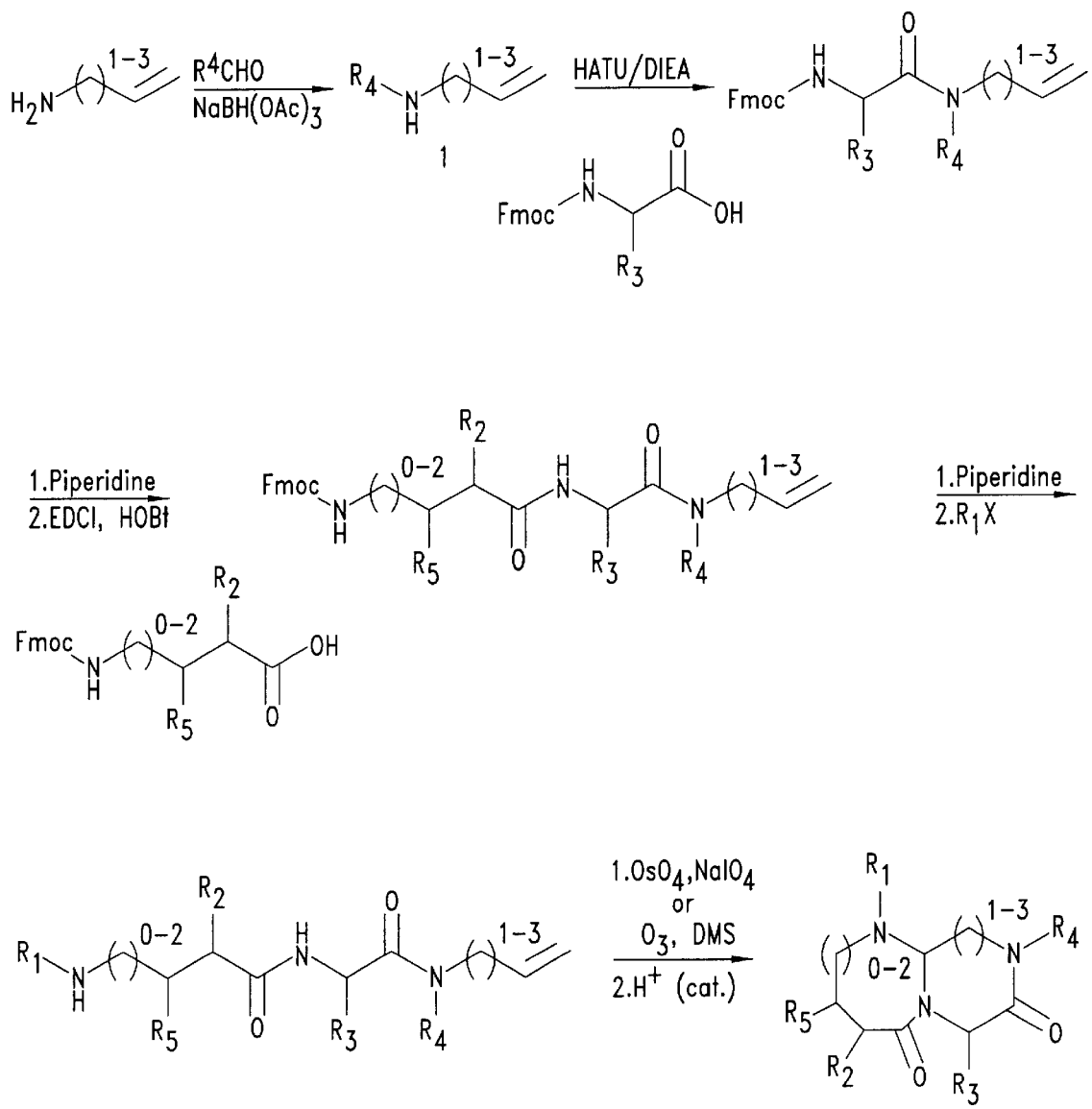
FIGS. 2–9 illustrate representative reaction schemes for the synthesis of reverse-turn mimetics of this invention.
Figure 3:
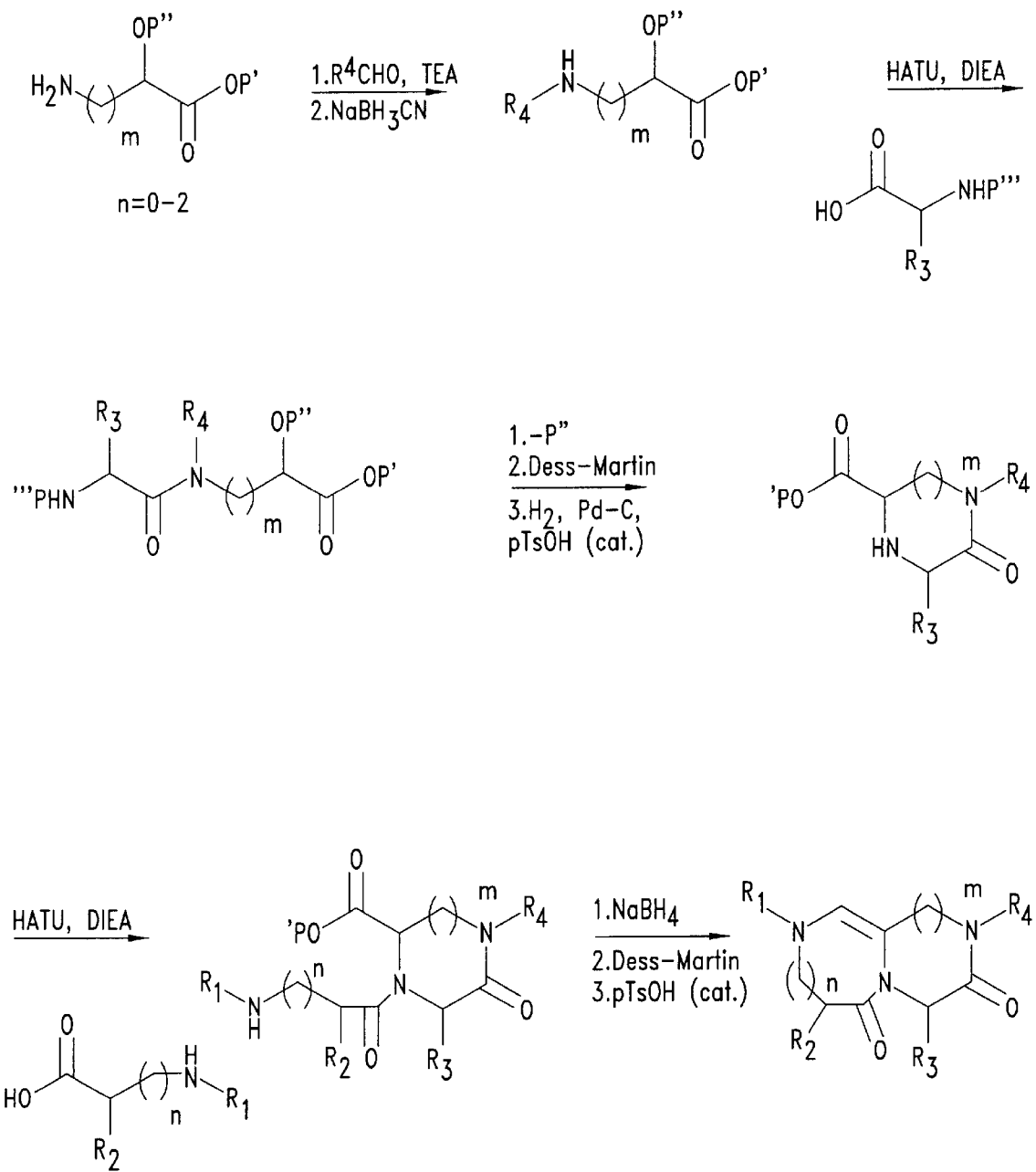
Figure 4:
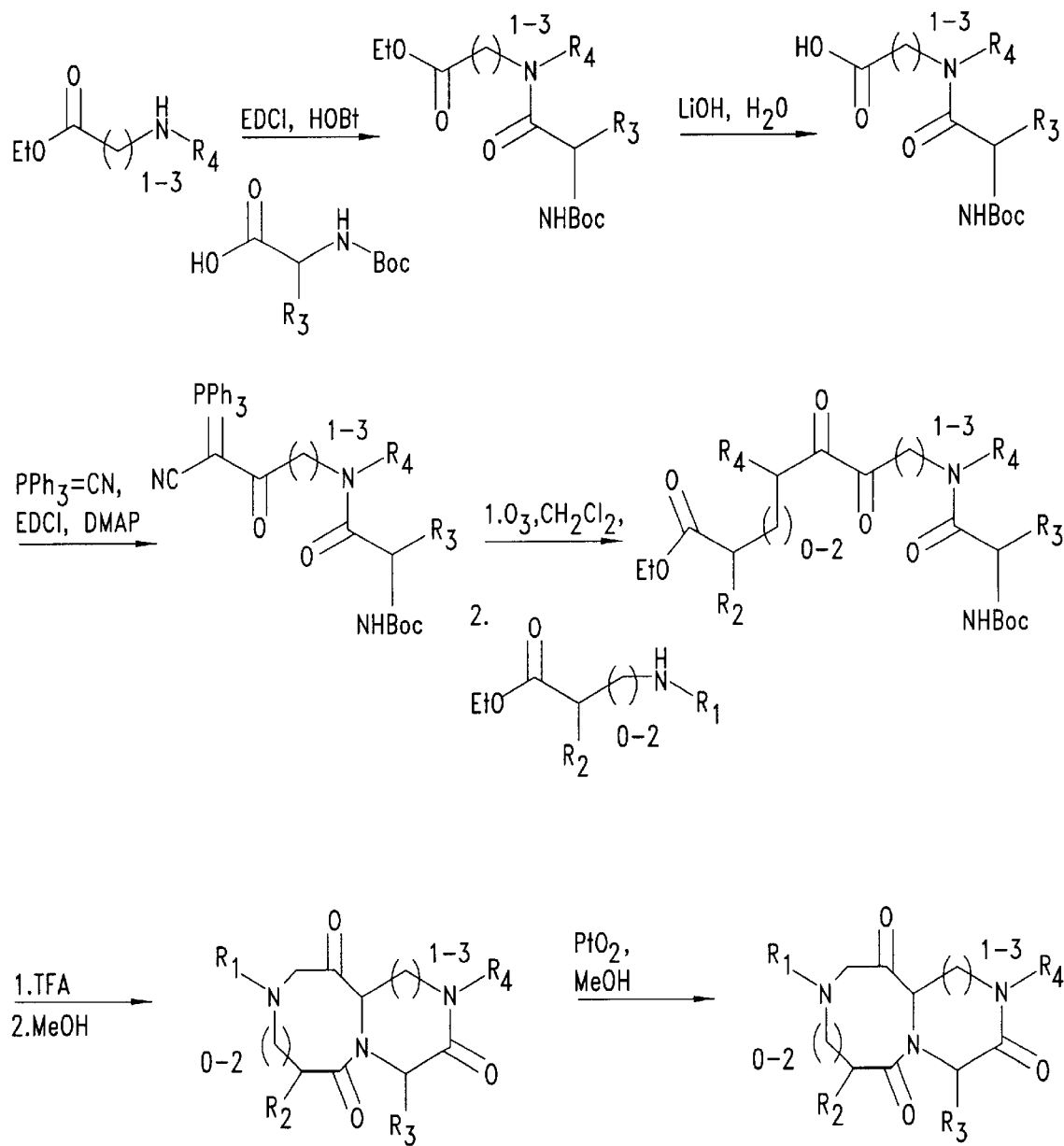
Figure 5:
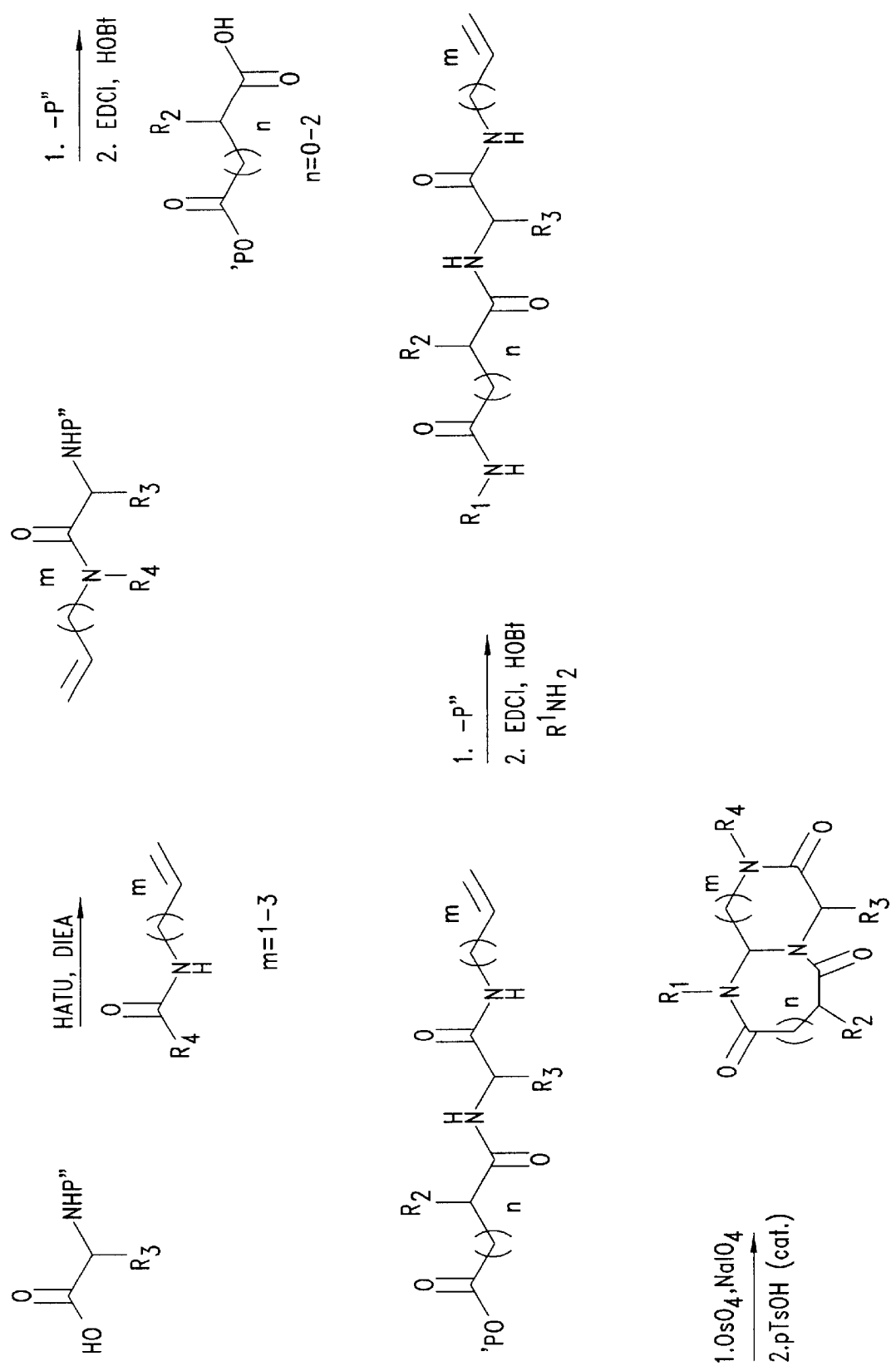
Figure 6:
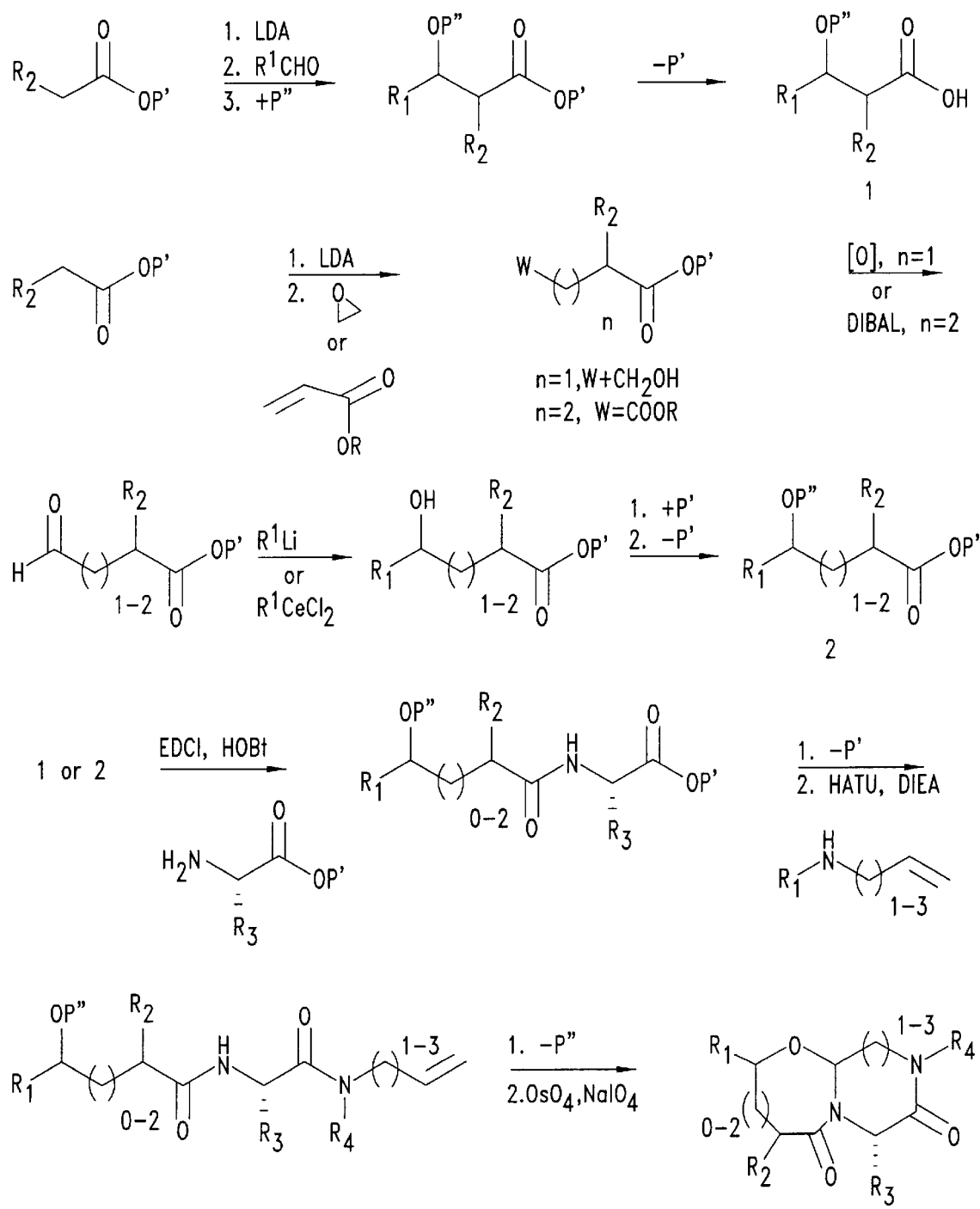
Figure 7:
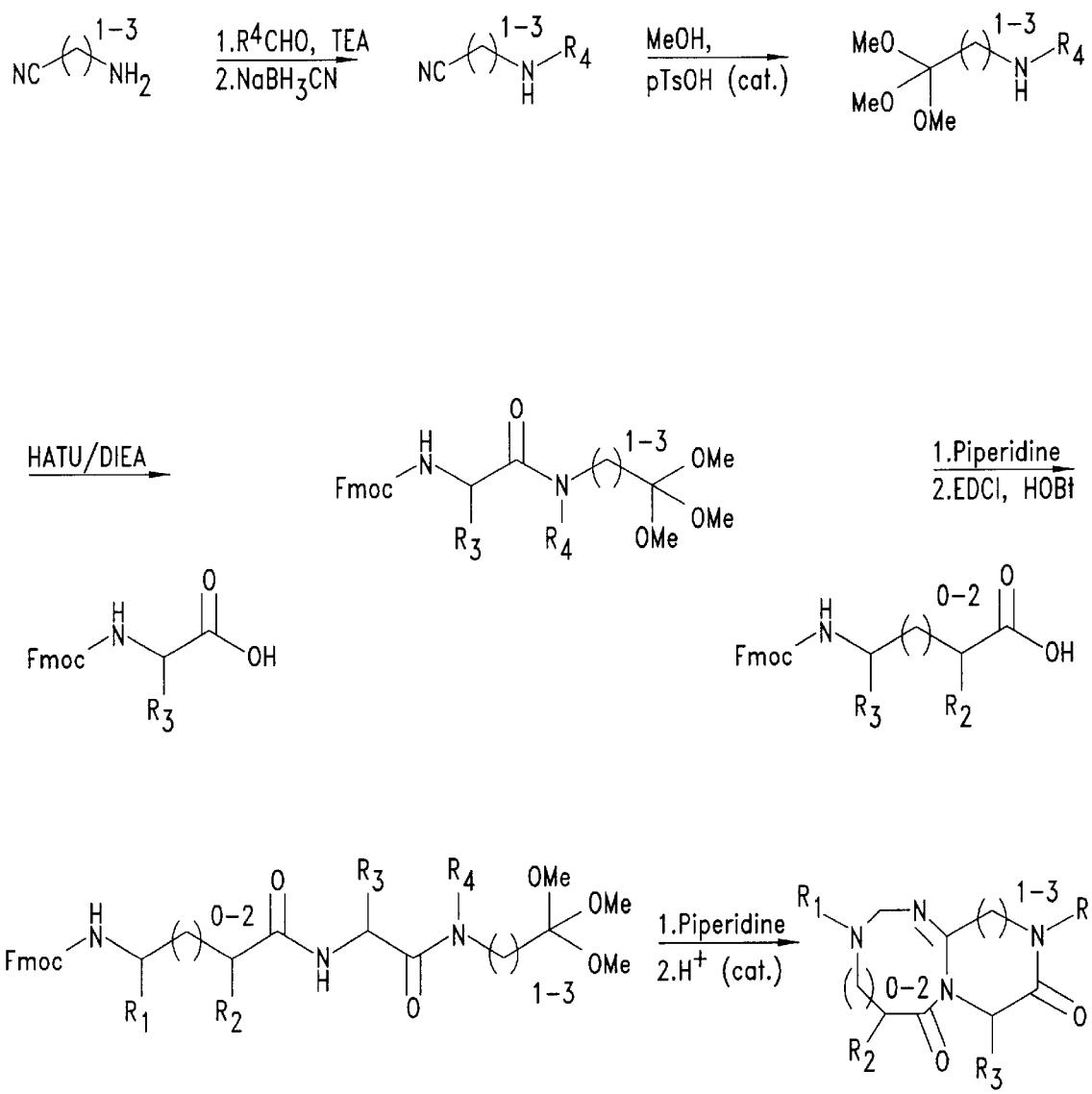

In a preferred embodiment, the reverse-turn mimetic of structure (Ia') may be made in solution according to the reaction scheme set forth in FIG. 2. In another preferred embodiment, the reverse-turn mimetic of structure (Ia') may be made on solid-phase according to the reaction scheme set forth in FIG. 8 and described in Example 8. In a more preferred embodiment, the reverse-turn mimetic of structure (Ia') may be made on solid-phase according to the reaction scheme set forth in FIG. 9 and described in Example 10.

The reverse-turn mimetics of structures (I") through (I"''") may be made by techniques analogous to the modular component synthesis disclosed above, but with appropriate modifications to the component pieces. More specifically, the reverse-turm mimetics of structures (I") through (I"''") may be made by the reaction schemes set forth in FIGS. 3–7. In particular, the reverse-turn mimetics of structures (Ib"), (Ia'''), (Ia''''), (Ia''''') and (Ib''''') may be made by the representative reaction schemes set forth in FIGS. 3, 4, 5, 6 and 7, respectively.

In another aspect of this invention, libraries containing reverse-turn mimetics of the present invention are disclosed. Once assembled, the libraries of the present invention may be screened to identify individual members having bioactivity. Such screening of the libraries for bioactive members may involve, for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members which are capable of interacting with the target of interest are referred to herein as "bioactive library members" or "bioactive mimetics". For example, a bioactive mimetic may be a library member which is capable of binding to an antibody or receptor, which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields reverse-turn mimetics which are themselves biologically active, and thus useful as diagnostic, prophylactic or therapeutic agents, and may further be used to significantly advance identification of lead compounds in these fields.

Synthesis of the peptide mimetics of the library of the present invention may be accomplished using known peptide synthesis techniques, in combination with the first, second and third component pieces of this invention.) More specifically, any amino acid sequence may be added as any of the $R_1$, $R_2$, $R_3$, $R_4$ or $R_5$ moieties of the conformationally constrained reverse-turn mimetic. Preferably the amino acid sequence may be added as the $R_1$ or $R_4$ moieties. To this end, the mimetics may be synthesized on a solid support (such as polystyrene utilizing 4-hydroxymethylphenoxybutyrate as a linker) by known techniques (see, e.g., John M. Stewart and Janis D. Young, *Solid Phase Peptide Synthesis,* 1984, Pierce Chemical Comp., Rockford, Ill.; Atherton, E., Shepard, R. C. *Solid Phase Pepetide Synthesis: A Practical Approach;* IRL: Oxford, 1989) or on a silyl-linked resin by alcohol attachment (see Randolph et al., *J. Am Chem. Soc.* 117:5712–14, 1995).

In addition, a combination of both solution and solid phase synthesis techniques may be utilized to synthesize the peptide mimetics of this invention. For example, a solid support may be utilized to synthesize the linear peptide sequence up to the point that the conformationally constrained reverse-turn is added to the sequence. A suitable conformationally constrained reverse-turn mimetic which has been previously synthesized by solution synthesis techniques may then be added as the next "amino acid" to the solid phase synthesis (i.e., the conformationally constrained reverse-turn mimetic, which has at least two reactive sites, may be utilized as the next residue to be added to the linear peptide). Upon incorporation of the conformationally constrained reverse-turn mimetic into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained reverse-turn mimetic in solution using known solution coupling techniques.

In another aspect of this invention, methods for constructing the libraries are disclosed. Traditional combinatorial chemistry and parallel synthesis techniques (see, e.g., *The Combinatorial Index* Bunin, Academic Press, New York, 1998; Gallop et al., *J. Med. Chem.* 37:1233–1251, 1994) permit a vast number of compounds to be rapidly prepared by the sequential combination of reagents to a basic molecular scaffold. For example, the above disclosed synthesis may be carried out using the directed sorting technique of Nicolaou and coworkers (Nicolaou, Xiao et al. *Angew. Chem. Int. Ed.* 34: 2289–2291, 1995). Presently, equipment for this technique is commercially available from IRORI (La Jolla, Calif.). Alternatively, the above disclosed synthesis may be carried out by parallel synthesis using a 48- or 98-well plate format wherein each well contains a fritted outlet for draining solvents and reagents (*A Practical Guiide to Combinatorial Chemistry* Czarnik and DeWitt, Eds., American Chemical Society, Washington, D.C., 1997). Robbins (Sunnyvale, Calif.), Charybdis (Carlsbad, Calif.) and Bohdan (Chicago, Ill.) presently offer suitable equipment for this technique.

In a further aspect of this invention, methods for screening the libraries for bioactivity and isolating bioactive library members are disclosed. The libraries of the present invention may be screened for bioactivity by a variety of techniques and methods. Generally, the screening assay may be performed by (1) contacting a library with a biological target of interest, such as a receptor, and allowing binding to occur between the mimetics of the library and the target, and (2) detecting the binding event by an appropriate assay, such as by the colorimetric assay disclosed by Lam et al. (*Nature* 354:82–84, 1991) or Griminski et al. (*Biotechnology* 12:1008–1011, 1994). In a preferred embodiment, the library members are in solution and the target is immobilized on a solid phase. Alternatively, the library may be immobilized on a solid phase and may be probed by contacting it with the target in solution.

As mentioned above, the reverse-turn mimetics of the present invention are useful as bioactive agents, such as diagnostic, prophylactic, and therapeutic agents. The opiate receptor binding activity of representative reverse-turn mimetics is presented in Example 9. In this example, the reverse-turn mimetics of this invention were found to effectively inhibit the binding of a radiolabeled enkephalin derivative to the $\delta$ and $\mu$ opiate receptors. The data demonstrates the utility of these reverse-turn mimetics as receptor antagonists and as potential analgesic agents. In a further embodiment, the integrin binding activity of representative reverse-turn mimetics is presented in Example 11. In this example, the reverse-turn mimetics were found to effectively displace CS1 peptide from Ramos cells. The data thus indicate the ability of reverse turn mimetics to antagonize $\alpha_4\beta_1$ integrins and serve as potential anti-inflammatory agents.

In another aspect, the present invention encompasses pharmaceutical compositions prepared for storage or administration which comprise a therapeutically effective amount of a compound of the present invention in a pharmaceutically acceptable carrier or diluent. Therapy with inhibitors of cell adhesion is indicated for the treatment and prevention of a variety of inflammatory conditions, particularly rheumatoid arthritis, inflammatory bowel disease and asthma. Those experienced in this field are readily aware of the circumstances requiring anti-inflammatory therapy. In addition, therapy with inhibitors of cell adhesion are indicated for any condition in which an excess of integrin-mediated cell adhesion is a contributing factor, such as, for example, atherosclerosis.

The "therapeutically effective amount" of a compound of the present invention will depend on the route of administration, the type of warm-blooded animal being treated, and the physical characteristics of the specific animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use, including diluents, are well known in the pharmaceutical art, and are described, for example, in *Remingtons Pharmaceiutical Sciences,* Mack Publishing Co. (Gennaro Ed. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

Compounds of the present invention are useful for prevention and treatment of any condition in which an excess of integrin-mediated cell adhesion is a contributing factor. In particular, the compounds of the present invention are useful as agents for the prevention and treatment of inflammation and related conditions. In the practice of the methods of this invention, a composition containing a therapeutically effective amount of a compound of this invention is administered to a warm-blooded animal in need thereof. For example, the compounds of this invention may be administered to a warm-blooded animal that has been diagnosed with, or is at risk of developing a condition selected from rheumatoid arthritis, atherosclerosis, Alzheimer's disease, AIDS dementia, ARDS, asthma, allergies, inflammatory bowel disease, CNS inflammation, atopic dermatitis, type I diabetes, encephalitis, myocardial ischemia, multiple sclerosis, meningitis, nephritis, restenosis, retinitis, psoriasis, stroke and tumor metastasis.

Multiple sclerosis (MS) is a progressively debilitating autoimmune disease of the central nervous system. Presently the exact antigen triggering the immune response is unknown. However, macrophages appear to attack and initiate the destruction of the fatty myelin sheaths surrounding nerve fibers in the brain. In an animal model of MS (experimental allergic encephalomyelitis) murine monoclonal antibodies to $\alpha_4\beta_1$ blocked adhesion of the leukocytes to the endothelium, and prevented inflammation of the central nervous system and subsequent paralysis of the animals (Yednock, Cannon et al. *Nature* 356: 63–6, 1992).

The compounds of the present invention may be used singularly, as a combination of two or more compounds, or in combination with other known inhibitors of inflammation. For example the compounds of this invention may be used therapeutically with corticosteroids, non-steroidal anti-inflammatory agents, COX-2 inhibitors, matrix metalloprotease inhibitors or lipoxygenase inhibitors. The compounds of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, intranasal, intrarectal or intramuscular form, all using forms well known to those of ordinary skill in the pharmaceutical arts. The compounds may be administered intraocularly or topically as well as orally or parenterally.

The compounds of this invention may be administered by inhalation, and thus may be delivered in the form of an aerosol spray from pressurized packs or nebulizers. The compounds may also be delivered as powders which may be formulated and the powder composition may be inhaled with the aid of an insufflation powder inhaler device. A preferred delivery system for inhalation is the metered dose inhalation aerosol, which may be formulated as a suspension or solution of a compound of the invention in suitable propellants, such as fluorocarbons or hydrocarbons. Another preferred delivery system is the dry powder inhalation aerosol, which may be formulated as a dry powder of a compound of this invention with or without additional excipients.

The compounds of the invention can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of this invention may also be delivered by the use of monoclonal antibodies as individual carriers to which the compound molecules are coupled. The integrin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartarnide-phenol, or polyethyleneoxide-polylysine substituted with palmitoyl residues. Furthermore, the integrin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dose and method of administration can be tailored to achieve optimal efficacy but will depend on such factors as weight, diet, concurrent medication and other factors which those skilled in the medical arts will recognize. When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions.

Tablets suitable for oral administration of active compounds of the invention can be prepared as follows:

|  | Amount-mg | | |
| --- | --- | --- | --- |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

An intravenous dosage form of the above-indicated active compounds may be prepared as follows:

| Active Compound | 0.5–10.0 mg |
| --- | --- |
| Sodium Citrate | 5–50 mg |
| Citric Acid | 1–15 mg |
| Sodium Chloride | 1–8 mg |
| Water for Injection (USP) | q.s. to 1 mL |

Utilizing the above quantities, the active compound is dissolved at room temperature in a previously prepared solution of sodium chloride, citric acid, and sodium citrate in Water for Injection (USP, see page 1636 of United States Pharmacopoeia/National Formulary for 1995, published by United States Pharmacopoeia Convention, Inc., Rockville, Md., copyright 1994).

The following examples are provided for purposes of illustration, not limitation.

EXAMPLES

Example 1

Synthesis of Component Pieces

In this example, the synthesis of representative component pieces which may be combined to form the reverse-turn mimetics of the present invention is disclosed.

A. Representative First Component Pieces

A first component piece having the following structure 1 was utilized:

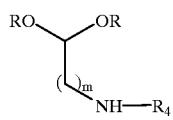

where $R_4$ is as defined above, and R represents a protective group suitable for use in peptide synthesis. Suitable R groups include alkyl groups and, in a preferred embodiment, R is a methyl group.

Generally, the first component piece is prepared by N-alkylation of an amine with a dialkylacetal of a 2-haloethanal. The synthesis of a representative first component piece from phenethylamine and the dimethylacetal of 2-bromoethanal is depicted schematically below.

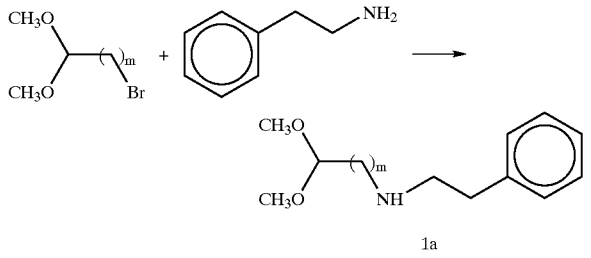

1a

In the procedure, 24 ml (3.43 ml, 20.3 mmol) of bromide and 2.8 ml (2.71 g. 22.3 mmol) phenethylamine was added 40 ml freshly distilled THF in a 150 ml argon charged round-bottom flask equipped with a reflux condenser. The reaction was heated at a gentle reflux for 24 hours, then volatiles were removed under reduced pressure and the residue was dissolved in 200 ml dichloromethane. The organic layer was washed with 2×100 ml sat. aq. sodium bicarbonate, sat. aq. sodium chloride, and dried over anhydrous sodium sulfate. Volatiles were removed under reduced pressure and the residue dried for 3 hrs. under high vacuum to yield 3.5 g (83%) first component piece 1a (m=1) as a light brown oil used without further purification.

B. Representative Second Component Pieces

A representative second component piece of this invention is a reactive N-protected amino acid having an activated carboxylic acid group, or an azido derivative of an amino acid, as represented by the following structure 2:

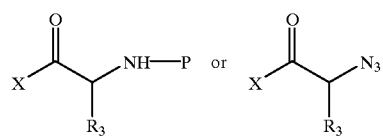

where $R_3$ is as defined above, P is an amino protective group suitable for use in peptide synthesis, and X represents the leaving group of the activated carboxylic acid group. Preferred protective groups include t-butyl dimethylsilyl (TBDMS), BOC, FMOC, and Alloc (allyloxycarbonyl). N-Protected amino acids are commercially available. For example, FMOC amino acids are available from a variety of sources. The conversion of these compounds to the second component pieces of this invention may be readily achieved by activation of the carboxylic acid group of the N-protected amino acid. Suitable activated carboxylic acid groups include acid halides where X is a halide such as chloride or bromide, acid anhydrides where X is an acyl group such as acetyl, reactive esters such as an N-hydroxysuccinimide esters and p-nitrophenyl esters, and other activated intermediates such as the active intermediate formed in a coupling reaction using a carbodiimide such as dicyclohexylcarbodiimide (DCC). Similarly, the corresponding azido derivative may be prepared by known techniques. In a preferred embodiment, X is hydroxyl for HATU (0-(7-azabenzotriaol-1-yl)-1,1,3,3-tetramethyluronium hexafluorophosphate) coupling, or is fluorine for silicon mediated coupling.

C. Representative Third Component Pieces

A representative third component piece of this invention is an α,β-unsaturated carboxylic acid or derivative thereof having the following structure 3:

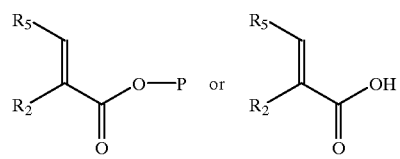

where $R_2$ and $R_5$ are as defined above, and P is a carboxylic acid protective group such as a methyl or t-butyl group. Such third component pieces may be obtained commercially, or synthesized from the commercially available aldehyde and the appropriate phosphorusylide according to the following reaction scheme:

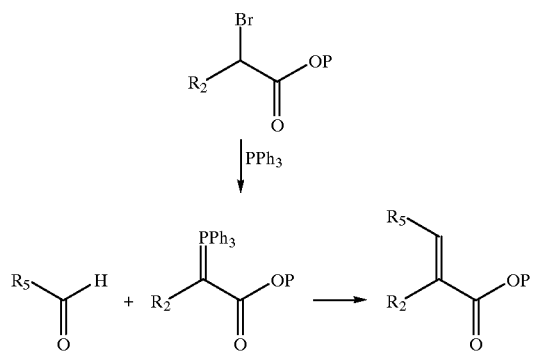

(see, Wadsworth and Emmons, *Org. Syn.* 45:44, 1965).

D. Representative Fourth Component Pieces

A representative fourth component piece of this invention is a primary amine having the following structure 4:

$$R_1-NH_2 \qquad 4$$

where $R_1$ is as defined above. Suitable fourth component pieces are commercially available from a variety of sources. Alternatively, the fourth component pieces may be readily prepared by standard organic synthetic techniques commonly utilized for the synthesis of primary amines.

Example 2

Combined First-Second Intermediates: The Coupling of First and Second Component Pieces The coupling of the component pieces to produce the reverse-turn mimetics of the present invention generally involve the formation of amide bonds. The amide bonds which link the pieces may be formed by standard synthetic peptide techniques and may be performed by either liquid or solid phase synthesis.

The coupling of the first and second component pieces provides, after deprotection, a combined first-second intermediate having the following structure 1-2:

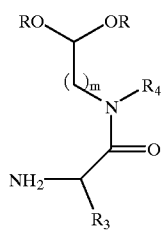

where R, $R_3$, and $R_4$ are as described above (in this example, R" of structure (I') is/are hydrogen).

The preparation of a combined first-second intermediate is accomplished by amide bond formation between the amine of a first component piece 1 and the activated carboxylic acid group of a second component piece 2 followed by N-deprotection. The synthesis of a representative combined first-second intermediate is depicted schematically below.

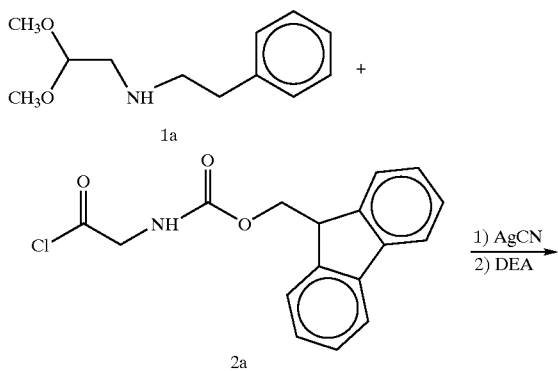

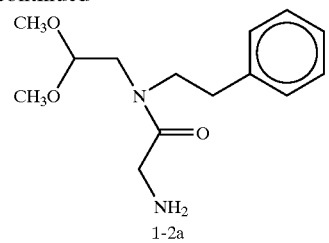

In the procedure, to 650 mg (3.17 mmol) first component piece 1a prepared as described in Example 1A and 1 g (3.17 mmol) FMOC-glycine chloride, 2a, 10 ml freshly distilled benzene in a 25 ml argon charged round bottom flask was added 937 mg (7 mmol) silver cyanide (AgCN), and the resulting reaction mixture was stirred vigorously for 48 hrs. The reaction was diluted to 25 ml w/ethyl acetate and filtered through a Celite plug. Volatiles were removed under reduced pressure and the residue was chromatographed using 20:80 ethyl acetate:hexane as the mobile phase over flash grade silica gel to yield 1.1 g (71%) of an amorphous solid.

To 400 mg (0.82 mmol) of the amorphous solid in 5 ml acetonitrile was added 1 ml diethylamine (DEA) dropwise and the resulting reaction mixture was stirred at room temperature for 2 hrs. The volatiles were removed under reduced pressure and the residue was chromatographed using 5% methanol saturated with ammonia 95% dichloromethane as the mobile phase over flash grade silica gel to yield 207 mg (95%) of a combined first-second intermediate, 1-2a, as a thick colorless oil.

Example 3

Combined Third-Fourth Intermediates: The Coupling of Third and Fourth Component Pieces The coupling of a third component piece with a fourth component piece provides a combined third-fourth intermediate. The combined third-fourth component piece is produced by amine bond formation resulting from the conjugate addition of the amine group of a fourth component piece 4 to the α,β-unsaturated carbonyl group of a third component piece 3.

The coupling of third and fourth component pieces provides, after deprotection, a combined third-fourth intermediate having the following structure 3-4:

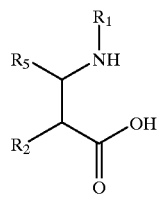

where $R_1$, $R_2$, and $R_5$ are as described above (in this example, n of structure (I') is O).

The preparation of a combined third-fourth intermediate is accomplished by amine bond formation between the primary amino group of a fourth component piece 4 and α,β-unsaturated carbonyl group of a third component piece 3 followed by O-deprotection. The synthesis of a representative combined third-fourth intermediate is depicted schematically below.

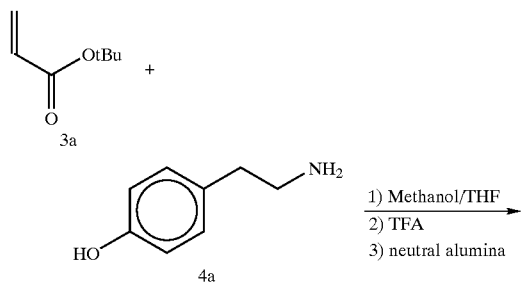

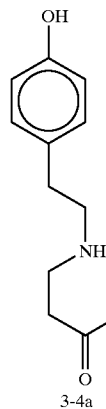

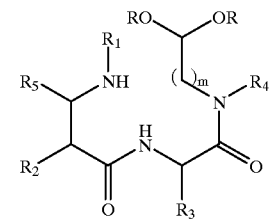

where R, $R_1$, $R_2$, $R_3$, $R_4$ and $R_5$ are as described above.

The synthesis of a representative combined first-second-third-fourth intermediate is depicted schematically below.

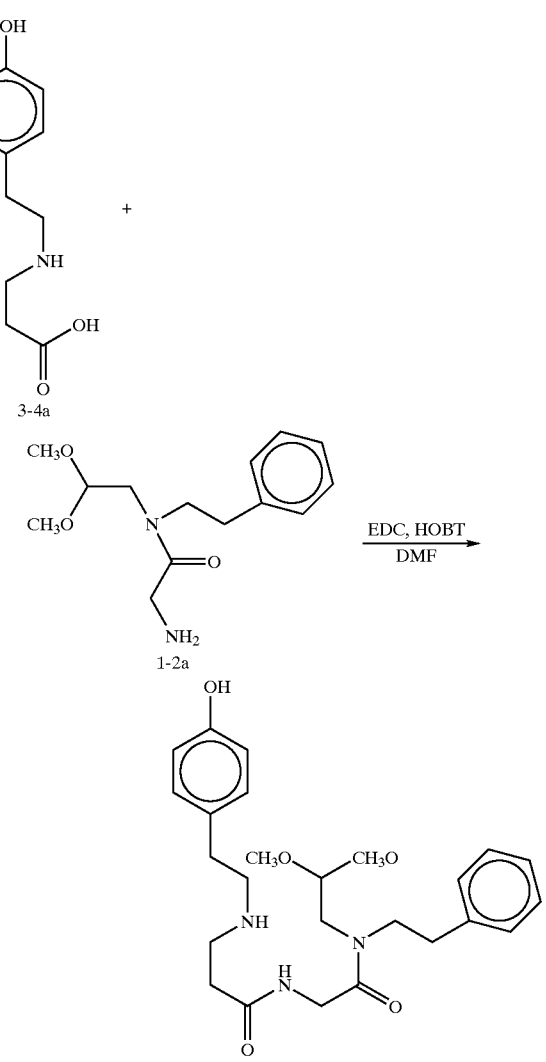

In the procedure, to 5 g of tyramine suspended in 40 ml freshly distilled tetrahydrofuran (THF) in an argon charged, 250 ml round-bottom flask was added methanol sufficient to dissolve the suspension. To the resulting solution was added 5.3 ml (4.67 g, 36.4 mmol) of t-butylacrylate dropwise over the course of 5 min, and the resulting reaction mixture was stirred overnight at room temperature. An additional 2 ml of t-butylactylate was added to consume the remaining starting material and the reaction was stirred an additional 4 hrs. Volatiles were removed under reduced pressure and the residue was chromatographed using 95:5 dichloromethane:ammonia saturated methanol:$NH_3$/MeOH as the mobile phase over flash grade silica gel to yield 6.6 g (68%) of the ester, a colorless oil which solidified upon overnight refrigeration. To a solution of 1 gram (3.77 mmol) of the ester in 20 ml dichloromethane at 0° C. was added 80 ml of cold trifluoroacetic acid (TFA) and the resulting reaction mixture was stirred with warming to room temperature over the course of 24 hrs. Volatiles were removed under reduced pressure to yield 950 mg of a clear oil. The end product was dissolved in 95:5 dichloromethane:methanol and slowly filtered through a pad of neutral alumina. Volatiles were removed from the filtrate to yield 750 mg of 3-4a as an amorphous solid.

Example 4

Combined First-Second-Third-Fourth Intermediates:
The Coupling of Combined First-Second and Third-Fourth Intermediates The coupling of a combined first-second intermediate with a combined third-fourth intermediate provides a combined first-second-third-fourth intermediate. The combined first-second-third-fourth intermediate is produced by amide bond formation resulting from the coupling of the amine group of a combined first-second intermediate 1-2 to the carboxylic acid group of a combined third-fourth intermediate 3-4. The combined first-second-third-fourth intermediate has the following structure 1-2-3-4:

In the procedure, 212 mg (1.0 mmol) 3-4a, 270 mg (1.01 mmol) 1-2a, and 136 mg (1.01 mmol) 1-hydroxybenzotriazole hydrate (HOBT) were dissolved in 10 ml dimethylformamide (DMF) and cooled to 0° C. To this solution was added 290 mg (1.52 mmol, 1.5 eq) 1-(3-dimethylaminopropyl)-3-ethylcarbodiimide (EDC) and the resulting reaction mixture was stirred and warmed to room temperature over the course of 24 hours. The DMF was removed under reduced pressure and the residue was redissolved in 200 ml ethyl acetate. The ethyl acetate layer was washed with saturated aqueous sodium bicarbonate, water, and dried over anhydrous sodium sulfate. Volatiles were removed under reduced pressure and the residue was chromatographed using 95:5 dichloromethane:ammonia saturated methanol as eluent over flash-grade silica gel to yield 310 mg (0.68 mm 67%) 1-2-3-4a as a thick colorless oil.

Example 5

The Synthesis of a Representative Reverse-Turn Mimetic: Cyclization of a Combined First-Second-Third-Fourth Intermediate The cyclization of a combined first-second-third-fourth intermediate provides a reverse-turn mimetic of the present invention. The combined first-second-third-fourth intermediate 1-2-3-4 is cyclized by treatment with camphorsulfonic acid (CSA) or, in a preferred embodiment, TMSOTF (at 0° C.) to provide a reverse-turn mimetic having the following structure (Ia):

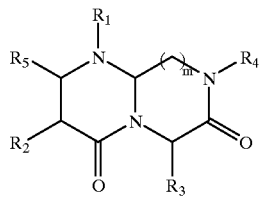

(Ia)

where $R_1$, $R_2$, $R_3$, $R_4$, and $R_5$ are as described above.

The synthesis of a representative reverse-turn mimetic of the present invention is depicted schematically below.

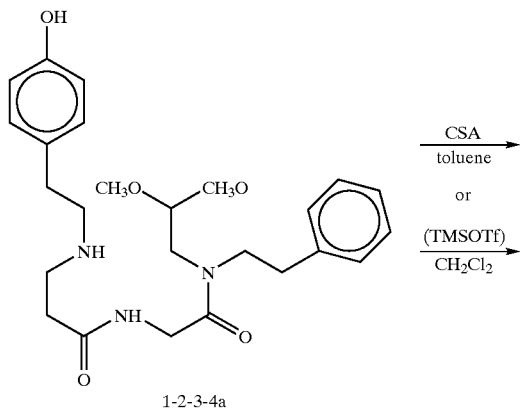

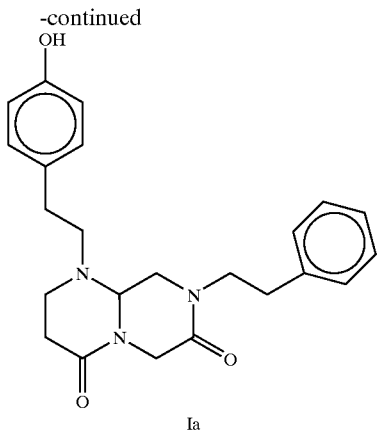

In the procedure, 0.5 g (2.4 mmol) camphorsulfonic acid (CSA) was azeotroped with 3–15 ml portions of freshly distilled toluene and dried under vacuum at 40° C. for 3 hrs in a 100 ml round-bottom flask equipped with a reflux condenser. Then 20 ml of freshly distilled toluene was added and the CSA solution was heated to a vigorous reflux. To this refluxing CSA solution was added a solution of 50 mg (0.11 mmol) 1-2-3-4a in 20 ml of freshly distilled toluene by syringe pump over the course of 1 hr. The resulting reaction mixture was refluxed for 12 hrs, cooled to room temperature and diluted to 200 ml ethylacetate. The organic layer was washed with 2–75 ml portions of saturated aqueous sodium bicarbonate, 75 ml saturated aqueous sodium chloride, and dried over anhydrous sodium sulfate. Volatiles were removed under reduced pressure to yield 22 mg of Ia as a glassine solid. The crude product was triturated with 50/50 diisopropyl ether:hexane to remove non-polar impurities. The solid was then dissolved in dichloromethane and filtered to remove polar impurities. The residue upon evaporation was dried in vacuo for 24 hrs.

Example 6

Synthesis of a Representative Reverse-Turn Mimetic Salt

The reverse-turn mimetics of the present invention are nitrogen bases and may, therefore, be converted to their corresponding salts by treatment with various acids. In this example, the preparation of a representative salt of a reverse-turn mimetic is described.

The 2,4-dinitrobenzoic acid salt of reverse-turn mimetic Ia, prepared as described in Example 5, was obtained by treatment of the reverse-turn mimetic with the acid in aqueous methanol. In the procedure, 5 mg (12.7 μmol) Ia was dissolved in 3 ml of 80/20 methanol:water and cooled to 0° C. To this solution was added 2.70 mg (12.7 μmol, 1.0 eq) 2.4 dinitrobenzoic acid, and the resulting solution stirred until it became homogenous. Volatiles were removed under reduced pressure and the residue was dried in vacuo for 24 hrs. The residue was taken up in warm water and filtered to remove insoluble impurities. The solution was then lyophilized to give the salt, 5.

Example 7

Synthesis of a Representative Reverse-Turn Mimetics

This example illustrates the synthesis of further representative reverse-turn mimetics of this invention.

Synthesis of structure (6):

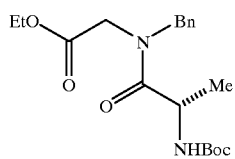

To a stirred solution of N-benzylglycine ethyl ester (1.93 g, 10 mmol) in THF (50 mL) was added Boc-Ala-OH (1.9 g, 10 mmol), followed by HOBt (1.62 g, 12 mmol) and EDCI (2.3 g, 12 mmol) at room temperature ("rt"). The resulting solution was stirred at rt for 5 hours ("h"). After dilution with EtOAc (100 mL), the solution was washed with 1N HCl (50 mL), sat. NaHCO$_3$ (50 mL), and brine (50 mL); it was dried (MgSO$_4$), passed through a short pad of SiO$_2$, and concentrated to give an oil in quantitative yield. TLC showed that the product was pure enough for use in the next reaction without further purification. TLC R$_f$ 0.6 (hexane:EtOAc=5:5); $^1$H NMR (CDCl$_3$) {the spectrum was assigned as 2:1 mixture of rotamers} δ 1.24 (two t, 3H, J=6.5 Hz), 1.35 and 1.36 (two d, 3H, J=6.5 Hz), 1.42 and 1.43 (two s, 9H), 3.80 (dd, 1H, J=18 Hz), 4.15 (q, 2H, J=6.5 Hz), 4.40 (dd, 1H), 4.65 (ABq, 2H, J=16.5 Hz), 4.80 (m, 1H), 5.40 (two d, 1H, J=8 Hz, NH), 7.1–7.3 (m, 5H, phenyl); MS ES+365.1 (M+H$^+$).

Synthesis of structure (7):

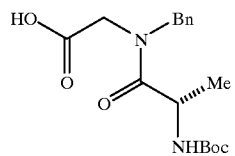

To a stirred solution of 3.8 g of crude ethyl ester (6) in THF/H$_2$O (50/50 mL) was added LiOH H$_2$O (1 g) at rt. After 30 min stirring at rt, the solution was washed with Et$_2$O (50 mL) and aqueous phase was acidified by 6N HCl (pH 2), and extracted with EtOAc (3×100 mL). The combined organic extracts were dried (MgSO$_4$), passed through a short pad of SiO$_2$, and concentrated to provide a foam in quantitative yield. The product was used for the next reaction without further purification. $^1$H NMR (CDCl$_3$) {mixture of rotamers} δ 1.33 (two d, 3H, J=7 Hz), 1.41 (two s, 9H), 3.8–4.8 (set of m, 5H), 5.70 (two d, 1H, J=8 Hz, NH), 7.2–7.6 (m, 5H, phenyl).

Synthesis of structure (8):

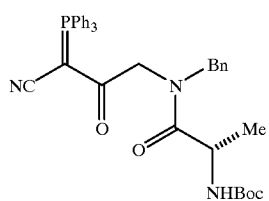

To a stirred solution of 3.4 g of acid (7) and cyanomethylene triphenylphosphorane (4.1 g, 12 mmol) in dichloromethane (100 mL) was added sequentially DIEA (5 mL, 30 mmol), DMAP (250 mg, 2 mmol), and EDCI (2.9 g, 15 mmol) at rt. After 12 h stirring, the solution was concentrated, and the resulting residue was taken up in 1N HCl (100 mL) and extracted with EtOAc (3×100 mL). The combined extracts were washed with sat. NaHCO$_3$ (100 mL), dried (MgSO$_4$), passed through a short pad of SiO$_2$, and concentrated. The crude product was purified by flash chromatography (hexane:EtOAc=50:50 to 30:70 to 20:80) to provide a foamy solid (4.40 g, 71%). TLC R$_f$ 0.5 (EtOAc); $^1$H NMR (CDCl$_3$) {mixture of rotamers} δ 1.28 (two d, 3H, J=6.5 Hz), 1.44 (two s, 9H), 4.2–4.7 (set of m, 5H), 5.5 (two d, 1H, J=8 Hz, NH), 7.2 (m, 5H), 7.5–7.8 (m, 15H); MS ES+m/z 520.3, 620.3 (M+H$^+$).

Synthesis of structure (9):

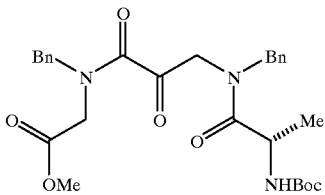

To a stirred solution of the phosphorane (8) (310 mg, 0.5 mmol) in dichloromethane (5 mL) was bubbled O$_3$ at −78° C. for 15 min until solution became greenish blue; TLC showed complete consumption of the starting material. After bubbling Ar to remove excess ozone from this solution, N-benzylglycine ethyl ester (100 mL) was added, and the solution was stirred at −78° C. for 30 min. After concentration, the residue was dissolved in EtOAc (50 mL), washed with 1N HCl (20 mL), sat. NaHCO$_3$ (20 mL), brine (20 mL), dried (MgSO$_4$), and concentrated again. The crude product was purified by flash chromatography (hexane:EtOAc=90:10 to 80:20 to 70:30 to 60:40) to provide an oil (105 mg, 39%). TLC R$_f$ 0.42 (hexane:EtOAc=60:40); $^1$H NMR (CDCl$_3$) {the spectrum was assigned as a 1:1 mixture of rotamers} δ 1.25 (two t, 3H, J=7 Hz), 1.31 and 1.38 (two d, 3H, J=7 Hz), 1.41 and 1.43 (two s, 9H), 3.8–4.8 (set of m, 11H), 5.5 (two d, 1H, NH), 7.2–7.4 (m, 5H). MS ES+m/z 440.3, 540.3 (M+H+).

Synthesis of structure (10):

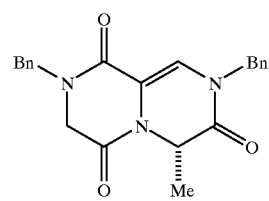

A solution of 100 mg ketoamide (9) (0.18 mmol) in 0.5 mL dichloromethane was treated with 0.5 mL TFA at rt for 30 min. After concentration, the residue was dissolved in MeOH (2 mL) and treated with ZnCl$_2$ (6 mg) and NaBH$_3$CN (15 mg) at rt for overnight 13 h). After concentration, the residue was taken up in sat. NaHCO$_3$ (20 mL), extracted with EtOAc (2×20 mL). The combined organic extracts were dnred (MgSO$_4$), concentrated to an oil, and purified by preparative TLC (hexane:EtOAc=60:40) to provide a glassy solid (52 mg, 77%). (The enamine proved resistant to reduction by this method.) TLC R$_f$ 0.58 (EtOAc); $^1$H NMR (CDCl$_3$) δ 1.41 (d, 3H, J=6.5 Hz, CHCH$_3$), 3.93 (ABq, 2H, J=18 Hz, CH2 in Gly), 4.46 and 4.75 (ABq, 1H each, J=14.5 Hz, CH$_2$Ph), 4.76 (ABq, 2H, J=14 Hz, CH$_2$Ph), 5.22 (q, 1H, J=7 Hz, CHCH$_3$), 6.83 (s, 1H, =CH), 7.33 (m, 10H, phenyls); $^{13}$C NMR (CDCl$_3$) δ 16.63, 49.59, 49.66, 49.84, 50.98, 111.92, 119.16, 128.07, 128.22, 128.29, 128.52, 128.94, 128.97, 134.78, 134.43, 157.96, 160.67, 165.33. MS ES+m/z 376.3 (M+H$^+$).

Synthesis of structure (11):

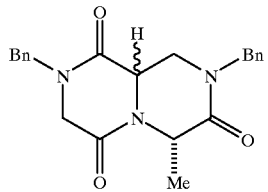

(11)

A solution of 25 mg structure (10) (0.066 mmol) with PtO$_2$ (5 mg) in MeOH (2 mL) was stirred under H$_2$ atmosphere (20 atm) for 10 days. After concentration, the residue was purified by preparative TLC (hexane:EtOAc=60:40 to 50:50) to yield a pale yellow oil (14 mg, 56%) with starting material (10 mg). TLC Rf 0.49 (EtOAc); $^1$H NMR (CDCl$_3$) δ 1.14 (d, 1.5H, J=7 Hz, CHCH$_3$), 1.52 (d, 1.5H, J=7 Hz, CHCH$_3$), 3.2–4.8 (set of m, 10H), 7.33 (m, 10H, phenyls); MS ES+m/z 378 (M+H$^+$). RP-HPLC analysis: C-18; A: 0.1% TFA (aq); B 0.1% TFA (CH$_3$CN); gradient: 0–90%/ 40'; 254 nm tR 24.1' and 24.7' showed a 2:1 ratio.

Example 8

Synthesis of a Representative Reverse-Turn Mimetics

This example further illustrates the syntheses of reverse-turn mimetics of this invention. Specifically, the preparation of [4.4.0] bicyclic reverse-turn mimetics was carried out in solution phase (Method A) and on solid phase (Methods B and C). Structures of representative mimetics are given in Table 2. The solid phase syntheses of these reverse-turn mimetics demonstrate that libraries containing such members may be readily prepared.

Method A solution phase synthesis is analogous to the solid phase synthesis of Method B and was carried out essentially as illustrated in FIG. 2. The compounds were purified as in Method C, below.

Figure 8:
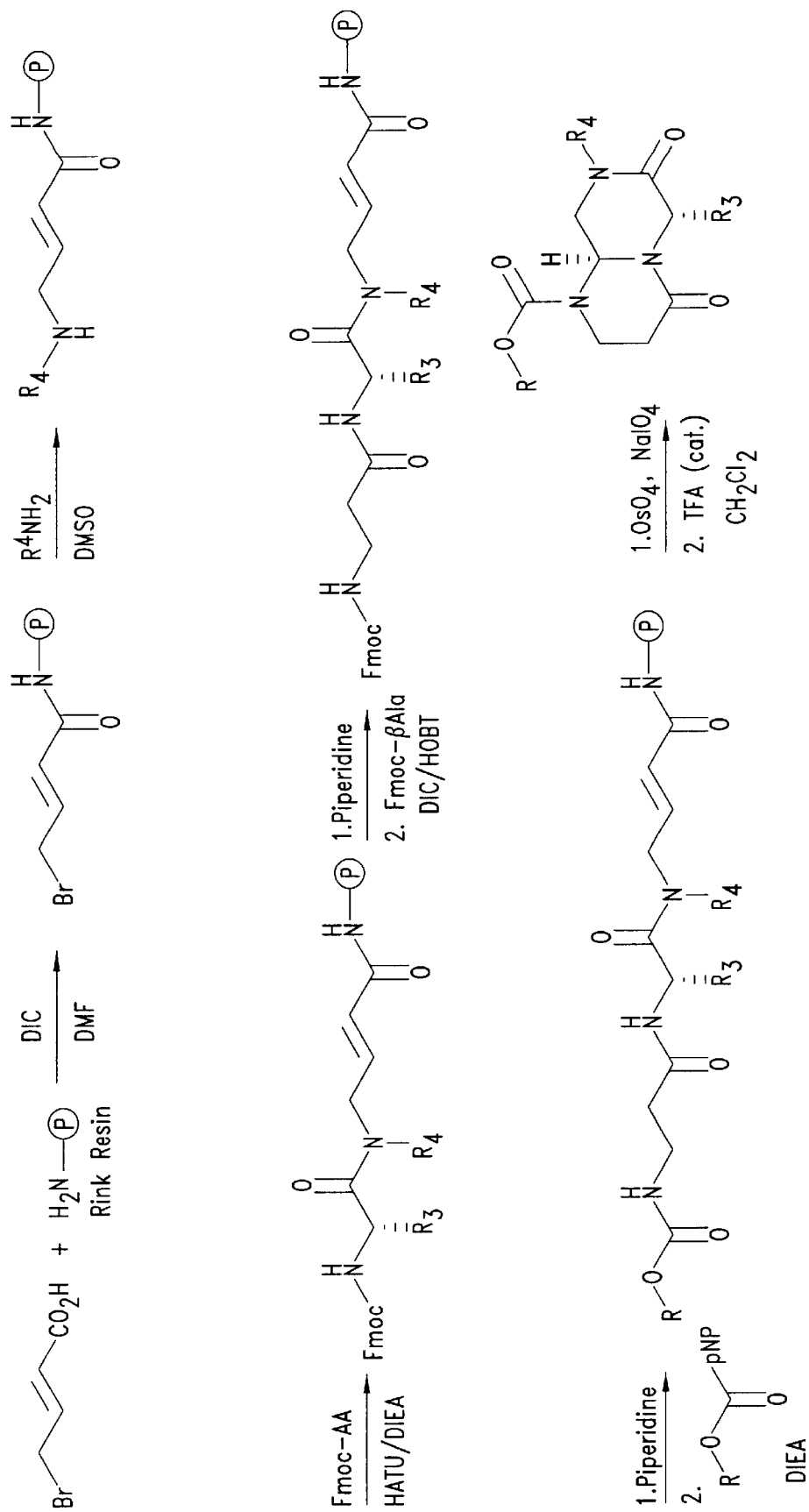

The solid phase synthesis of Method B is illustrated in FIG. 8. Referring to that figure, commercially available aminomethyl resin was reacted with excess 4-bromo-2-butenoic acid and DIC (diisopropylcarbdiimide) in DMF to give 4-bromo-2-butenamide resin. Substitution of the bromo group with a primary amine in DMSO gave the corresponding 4-alkylamino-2-butenamide resin. Standard peptide coupling procedures on solid phase were performed to give N-alkyloxycarbonyl-α-alkyl-β-alanyl-α-alkylglycyl-N'-alkylamino-2-butenamide resin. The reverse-turn mimetics were obtained by osmium tetroxide catalyzed periodate oxidation of the resin followed by the treatment of the resulting monocyclic product with a catalytic amount of TFA in dichloromethane. The crude products gave a single major peak by reverse-phase HPLC analysis.

Figure 9:
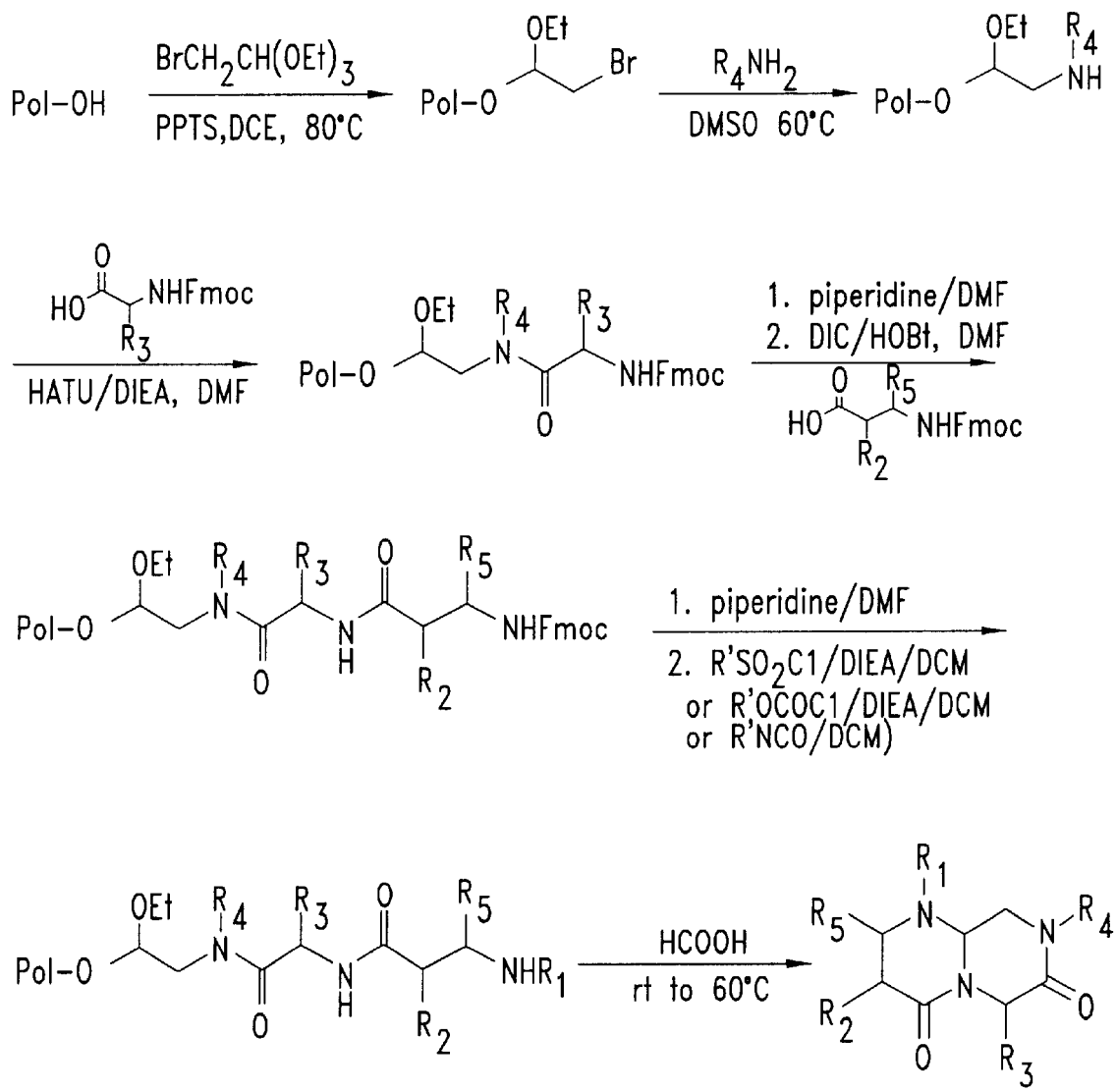

The solid phase sythesis of Method C is similar to Method B and is given in Example 11 and illustrated in FIG. 9. Selected compounds were purified by flash chromatography or preparative TLC on silica gel using suitable combinations of EtOAc and MeOH.

The mimetics were characterized as follows: Analytical C$_{18}$ reverse-phase HPLC was carried out using standard techniques (mobile phase: gradients of 0.1% in water and acetonitrile. By these methods, crude products synthesized on solid phase generally displayed purities of greater than 80%, and all purified compounds greater than 95%. Electrospray mass spectrometry was carried out using standard techniques. The observed value of the (M+H$^+$) ion is given for each compound in Table 2. $^1$H NMR was carried out on purified mimetics and spectra were assigned by a combination of COSY and ROESY experiments. All spectra were consistent with the structures indicated below, and displayed a conformation similar to a type I or type II β-turn.

TABLE 2

Representative Reverse-Turn Mimetics

| No. | R | R$_2$ | R$_3$ | R$_4$ | Method | MS (MH$^+$) |
|---|---|---|---|---|---|---|
| 12 | Bn | H | Me | Me | A, B | 332 |
| 13 | p-MeO—Ph(CH$_2$)$_2$ | H | H | Bn | A | 438 |
| 14 | p-MeO—Ph(CH$_2$)$_2$ | H | H | Phenethyl | A | 452 |
| 15 | p-OH—Ph(CH$_2$)$_2$ | H | H | Phenethyl | A | 438 |
| 16 | p-OH—Ph(CH$_2$)$_2$ | H | Bn | Pentyl | A | 494 |
| 17 | i-Bu | H | (CH$_2$)$_2$CO$_2$H | iBu | A | 398 |
| 18 | i-Bu | H | CH$_2$CO$_2$H | iBu | A | 384 |
| 19 | i-Bn | Bn | Bn | Pentyl | A | 554 |
| 20 | Bn | H | Me | Bn | B | 408 |
| 21 | Bn | H | Bn | Bn | B | 484 |
| 22 | Bn | H | Me | n-Bu | B | 374 |
| 23 | Bn | H | Bn | n-Bu | B | 449 |
| 24 | Bn | H | Me | i-Amyl | B | 388 |
| 25 | Bn | H | Bn | i-Amyl | B | 469 |

TABLE 2-continued

Representative Reverse-Turn Mimetics

| No. | R | $R_2$ | $R_3$ | $R_4$ | Method | MS (MH$^+$) |
|---|---|---|---|---|---|---|
| 26 | Bn | H | Bn | p-Cl—Bn | C | 518 |
| 27 | Bn | Ac—NH | Me | Me | C | 389 |
| 27 | Bn | Bz—NH | Me | Me | C | 451 |
| 29 | p-OH—Ph(CH$_2$)$_2$ | H | Bn | Phenethyl | C | 515 |
| 30 | p-OH—Ph(CH$_2$)$_2$ | H | Phenethyl | Pentyl | C | 508 |
| 31 | p-OH—Ph(CH$_2$)$_2$ | H | Bn | 2-Pyr(CH$_2$)$_2$ | C | 529 |
| 32 | Bn | H | t-BuO$_2$C—(CH$_2$)$_2$ | Me | B | 446 |
| 33* | Ph | H | Bn | c.HexCH$_2$ | C | 496 |
| 34* | Ph | Ac—NH | Me | Me | C | 395 |
| 35* | p-Tolyl | H | Bn | p-Cl-Bn | C | 538 |
| 36 | p-OH—Ph(CH$_2$)$_2$ | H | H | Pentyl | C | 404 |
| 37 | p-OH—Ph(CH$_2$)$_2$ | H | Me | Pentyl | C | 418 |
| 38 | p-OH—Ph(CH$_2$)$_2$ | H | MeS(CH$_2$)$_2$ | Pentyl | C | 478 |
| 39 | p-OH—Ph(CH$_2$)$_2$ | H | i-Bu | Pentyl | C | 460 |
| 40 | p-OH—Ph(CH$_2$)$_2$ | H | i-Pr | Pentyl | C | 446 |
| 41 | p-OH—Ph(CH$_2$)$_2$ | H | s-Bu | Pentyl | C | 460 |
| 42 | p-OH—Ph(CH$_2$)$_2$ | H | p-OH—PhCH$_2$ | Pentyl | C | 510 |
| 43 | p-OH—Ph(CH$_2$)$_2$ | H | Ph | Pentyl | C | 480 |
| 44 | p-OH—Ph(CH$_2$)$_2$ | H | p-Cl—PhCH$_2$ | Pentyl | C | 528 |
| 45 | p-OH—Ph(CH$_2$)$_2$ | H | p-NH$_2$—PhCH$_2$ | Pentyl | C | 509 |
| 46 | p-OH—Ph(CH$_2$)$_2$ | H | Bn | MeO(CH$_2$)$_3$ | C | 496 |
| 47 | p-OH—Ph(CH$_2$)$_2$ | H | Bn | i-Amyl | C | 494 |
| 48 | p-OH—Ph(CH$_2$)$_2$ | H | Bn | Heptyl | C | 522 |
| 49 | p-OH—Ph(CH$_2$)$_2$ | H | Bn | Bn | C | 514 |
| 50 | p-OH—Ph(CH$_2$)$_2$ | H | Bn | c.Hex CH$_2$ | C | 520 |
| 51 | p-OH—Ph(CH$_2$)$_2$ | H | Bn | 4-PyrCH$_2$ | C | 515 |
| 52 | p-OH—Ph(CH$_2$)$_2$ | H | Bn | i-Bu | C | 480 |
| 53 | p-OH—Ph(CH$_2$)$_2$ | H | Bn | 3,4-MeO-Phenethyl | C | 588 |
| 54 | p-OH—Ph(CH$_2$)$_2$ | H | Bn | N-Pyridone-(CH$_2$)$_3$ | C | 549 |
| 55 | p-OH—Ph(CH$_2$)$_2$ | H | p-OH—PhCH$_2$ | MeO(CH$_2$)$_3$ | C | 512 |
| 56 | p-OH—Ph(CH$_2$)$_2$ | H | p-OH—PhCH$_2$ | i-Amyl | C | 510 |
| 57 | p-OH—Ph(CH$_2$)$_2$ | H | p-OH—PhCH$_2$ | Heptyl | C | 538 |
| 58 | p-OH—Ph(CH$_2$)$_2$ | H | p-OH—PhCH$_2$ | Bn | C | 530 |
| 59 | p-OH—Ph(CH$_2$)$_2$ | H | p-OH—PhCH$_2$ | c.Hex CH$_2$ | C | 536 |
| 60 | p-OH—Ph(CH$_2$)$_2$ | H | p-OH—PhCH$_2$ | 4-PyrCH$_2$ | C | 531 |
| 61 | p-OH—Ph(CH$_2$)$_2$ | H | p-OH—PhCH$_2$ | i-Bu | C | 496 |
| 62 | p-OH—Ph(CH$_2$)$_2$ | H | p-OH—PhCH$_2$ | 3,4-MeO-Phenethyl | C | 604 |
| 63 | p-OH—Ph(CH$_2$)$_2$ | H | p-OH—PhCH$_2$ | N-Pyridone-(CH$_2$)$_3$ | C | 565 |
| 64 | p-OH—Ph(CH$_2$)$_2$ | H | p-OH—PhCH$_2$ | Phenethyl | C | 544 |
| 66 | p-OH—Ph(CH$_2$)$_2$ | H | Phenethyl | Phenethyl | C | 529 |
| 67 | p-OH—Ph(CH$_2$)$_2$ | H | p-OH—PhCH$_2$ | 2-Pyr(CH$_2$)$_2$ | C | 545 |
| 68 | p-OH—Ph(CH$_2$)$_2$ | H | Phenethyl | 2-Pyr(CH$_2$)$_2$ | C | 543 |
| 69 | p-OH—Ph(CH$_2$)$_2$ | H | i-Pr | i.Amyl | C | 446 |
| 70 | p-OH—Ph(CH$_2$)$_2$ | H | i-Bu | i.Amyl | C | 460 |

*—SO$_2$— replaces —OC(O)— in the R$_1$ side chain in this compound.

Example 9

Activity of a Representative Reverse-Turn Mimetic in Opioid Receptor Binding In this example, the binding activity of representative reverse-turn mimetics to the delta (δ) and mu (μ) opioid receptors as well as to a preparation of non-selective opioid receptors is described. The binding affinity of 5, the 2,4-dinitrobenzoic acid salt of reverse-turn mimetic of structure Ia (prepared as described in Example 6), and a variety of reverse-turn mimetics prepared as described in Example 8, was evaluated in these competitive radioligand binding assays.

A. Opiate (δ) Binding Activity

In this method, membranes were prepared from whole brains of male guinea pigs and equilibrated with 2 nM [$^3$H]DPDPE (D-pen$^3$, D-pen$^5$) enkephalin for 1 hour at 4° C. after which test substances were added and incubated for 4 hours at 25° C. Non-specific binding was determined in the presence of 0.3 μM naltrindole. Bound [$^3$H]DPDPE was separated from free radioligand by rapid filtration through glass fiber filtermats and subsequently washed 3. times. Filtermats were then counted in the LKB Betaplate to determine specifically bound [³H]DPDPE. (See Mosberg et al., "Structural Requirements for δ Opiate Receptor Binding," *Molec. Pharmacol.* 31:599–602, 1987.)

TABLE 3

Effect of Reference Compounds on [³H]DPDPE Bound (2nM)

| Compound | IC$_{50}$(nM) | Ki (nM) | Hill Coefficient |
|---|---|---|---|
| DAMGO | 4,800 | 1,200 | 1.08 |
| DPDPE | 5.5 | 1.3 | 0.86 |
| Naltrindole | 0.63 | 0.20 | 0.53 |
| U-50488 | 53,000 | 16,000 | 0.73 |

In this assay, the radioligand, [³H]DPDPE, was determined to have a K$_d$=0.65 nM with a B$_{max}$=12.6 fmol/mg protein and a specific binding of 60%. At a concentration of 10 μM, 5 was found to inhibit radioligand binding at the 60% level, and exhibited a K$_i$=1.7±0.3 μM and an IC$_{50}$=6.9±1.2 μM. These results are presented in FIG. 1 (o) which depicts the % inhibition of radioligand binding as a function of reverse-turn mimetic 5 concentration. Also, at a concentration of 10 μM, reverse-turn mimetic 16 was found to inhibit radioligand binding at the 92% level. These results demonstrate that reverse-turn mimetics 5 and 16, in particular, and the reverse-turn mimetics of the present invention, in general, effectively inhibit binding to the δ opiate receptor, and possess analgesic activity.

B. Opiate (μ) Binding Activity

In this method, membranes were prepared from whole brains of male guinea pigs and incubated with 2 nM [³H] DAMGO (D-Ala², N-methyl-phe⁴, gly-ol⁵)-enkephalin) for 2 hours at 25° C. Non-specific binding was determined in the presence of 0.5 μM DAMGO. Bound [³H]DAMGO was separated from free radioligand by rapid filtration through glass fiber filtermats and subsequently washed 3 times. Filtermnats were then counted in the LKB Betaplate to determine specifically bound [³H]DAMGO. (See Patricia et al., "Pharmacological profiles of fentanyl analogs at μ, δ and κ opiate receptors," *Eur. J. Pharmacol.* 213:219–225, 1992.)

TABLE 4

Effect of Reference Compounds on [³H]DAMGO Bound (2nM)

| Compound | IC$_{50}$(nM) | Ki (nM) | Hill Coefficient |
|---|---|---|---|
| DAMGO | 6.5 | 0.59 | 0.92 |
| DPDPE | 4.0 | 0.37 | 1.32 |
| Fentanyl | 14 | 1.2 | 0.99 |
| Naloxone | 9.3 | 0.76 | 1.09 |
| Naltrindole | 27 | 2.5 | 0.98 |
| Norbinaltorphimine | 280 | 26 | 1.13 |
| U-50488 | 6.1 | 0.59 | 0.70 |

In this assay, the radioligand, [³H]DAMGO, was determined to have a K$_d$=0.27 nM with a B$_{max}$=8.7 pmol/mg protein and a specific binding of 70%. At a concentration of 10 μM, 5 inhibited radioligand binding at the 64% level, and exhibited a K$_i$=0.64±0.08 μM and an IC$_{50}$=54±0.7 μM. These results are presented in FIG. 1 (●) which depicts the % inhibition of radioligand binding as a function of reverse-turn mimetic 5 concentration. Also, at a concentration of 10 μM, reverse-turn mimetic 16 was found to inhibit radioligand binding at the 98% level. These results demonstrate that reverse-turn mimetics 5 and 16, in particular, and the reverse-turn mimetics of the present invention, in general, effectively inhibit binding to the μ opiate receptor, and possess analgesic activity.

C. Opiate (Non-selective) Binding Activity

In this method (Childers et al. *Eur. J. Pharmacol.* 55: 11, 1979), membranes were prepared from rat cerebral cortex and incubated with [³H]naloxone (1 nM) and β-turn mimetics (30 μM–0.3 nM) for 40 min at 22° C. Following incubation, the membranes were rapidly filtered under vacuum through glass fiber filters (Filtermat A,. Wallac). The filters were then washed several times with an ice-cold buffer using a cell harvester (Tomtec). Bound radioactivity was measured with a scintillation counter (Betaplate, Wallac) using solid scintillant (MultiLex B/HS, Wallac). In same experiment, the reference compound (naloxone) was tested at eight concentrations in duplicate to obtain a competition curve in order to validate this experiment.

The specific radioligand binding to the receptors is defined as the difference between total binding and nonspecific binding determined in the presence of an excess of unlabelled ligand. Results were expressed as a percent of control specific binding obtained in the presence of β-turn mimetics. IC$_{50}$ values and Hill coefficients (nH) were determined by non-linear regression analysis of the competition curves. These parameters were obtained by Hill equation curve fitting. The inhibition constants (Ki) were calculated from the Chen Prusoff equation (Ki=IC$_{50}$/(1+L/K$_d$), where, L=concentration of radioligand in the assay, and K$_d$=affinity of the radioligand for the receptor).

In this assay, the radioligand, [³H]naloxone, was determined to have an IC$_{50}$=2.5 nM. Reverse turn mimetics, prepared and purified as described in Example 8, displayed specific binding of up to 99% at 1 μM concentration. Compounds 29 and 30 were determined to have IC$_{50}$s of 80 and 27 nM, respectively, with Hill coefficients of 0.9. These results demonstrate the mimetics 29 and 30, in particular, and the reverse-turn mimetics of the present invention, in general, effectively inhibit binding to the opioid receptor (non-selective), and possess analgesic activity.

Example 10

In Vivo Activity of a Representative Reverse-Turn Mimetic for Analgesic Activity In this example, the in vivo activity of a representative reverse-turn mimetic as an analgesic agent is presented. Compound 5, prepared as described in Example 6 (hereinafter referred to as "test compound"), was utilized in the mouse tail flick assay (PanLabs, Pharmascreen Test No. 10402A). In this assay, the time required to elicit a tail-flick response to radiant heat pain stimulus in a group of mice is measured as the pain threshold response.

Groups of five (3 test groups+1 saline control+1 morphine positive control) male ICR mice weighing 22 (±2) grams each were used. Each of these animals were pre-selected and elicited a tail flick response within 6–7.5 seconds after a focused beam of radiant heat was focused on the middle dorsal surface of the animal's tail. Specific amounts of the test compound (i.e., 10, 30 and 100 µg) were dissolved in 5 microliters (5 µl) saline containing 6% DMSA and administered intracerebroventricularly (ICV) to each animal. A saline-only solution was used as a negative control, with an ICV injection of 10 µg/5 µl/animal of morphine serving as a positive control.

At one minute post-ICV injection, the groups of mice were measured for tail flick response, with a maximum cut-off time of 15 seconds. The mean of the response time for each treatment groups was calculated for a comparison between pre-treatment ("0 time") and 1 minute post-treatment 1 ("1 min."). Prolongation 1 minute post-treatment of over 50% ("% Prolong.") was considered significant activity. The results of this experiment are presented in Table 5, and demonstrate that the test compound had significant analgesic activity (i.e., approximately 10%–15% the potency of morphine).

TABLE 5

In Vivo Tail Flick Assay

| Compound | Dose/5 µl | 0 Time | 1 Min. | % Prolong. |
|---|---|---|---|---|
| Saline | 0 | 6.9 | 6.7 | — |
|  |  | 6.9 | 7.5 | — |
|  |  | 6.1 | 6.2 | — |
|  |  | 6.5 | 6.3 | — |
|  |  | Avg. = 6.6 | Avg. = 6.7 | 2% |
| Morphine | 10 µg | 7.5 | >15 | — |
|  |  | 6.3 | >15 | — |
|  |  | 7.2 | >15 | — |
|  |  | 6.8 | >15 | — |
|  |  | Avg. = 7.0 | Avg. > 15 | 100% |
| Test Compound | 100 µmg | 6.5 | >15 | — |
|  |  | 6.3 | >15 | — |
|  |  | 6.5 | >15 | — |
|  |  | 6.8 | >15 | — |
|  |  | Avg. = 6.5 | Avg. > 15 | 100% |
|  | 30 µg | 6.5 | >15 | — |
|  |  | 6.7 | 7.2 | — |
|  |  | 7.2 | 6.3 | — |
|  |  | 6.3 | >15 | — |
|  |  | Avg. = 6.7 | Avg. > 15 | 63% |
|  | 10 µg | 6.5 | 7.5 | — |
|  |  | 7.2 | 7.5 | — |
|  |  | 6.9 | 6.7 | — |
|  |  | 6.2 | 6.8 | — |
|  |  | Avg. = 6.7 | Avg. 7.1 | 6% |

Example 11

Synthesis of Representative Reverse-Turn Mimetics

This example further illustrates the synthesis of reverse-turn mimetics of this invention. Specifically, the preparation of [4.4.0] bicyclic reverse-turn mimetics was carried out on solid phase by a method alternative to that of Example 8, method B. The method is outlined in FIG. 9.

Synthesis of 2-Bromo-1-ethoxy-ethyl-1-oxy-linked Resin (27)

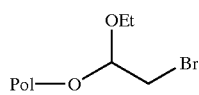
(27)

In general, a batch of resin (ArgogelOH or hydroxymethyl polystyrene) was refluxed in 1,2-dichloroethane (DCE) for 4 hours in the presence of 8 equivalents of bromoalkylaldehyde diethyl acetal and 2 equivalents of pyridinium p-toluenesulfonate (PPTS). In one instance, hydroxymethyl polystyrene (10.0 g, 0.7 mmol OH/g, 7 mmol) and 3.5 g of PPTS (14 mmol) were suspended in 200 ml of DCE. Then, a solution of 8.5 ml of 2-bromodiethoxyethane (ca. 56 mmol) in DCE (100 ml) was added with stirring and the reaction mixture was heated at reflux (approx. 80° C.). After 4 hours the resin was filtered off and washed with 100 mL dimethylformamide (DMF), 50 mL dimethylsulfoxide (DMSO), 100 mL DMF, 200 mL dichloromethane (DCM), 50 mL 1,4-dioxane and finally with 100 mL methanol. After drying, 11.73 g, of resin 27 was obtained. Bromine analysis indicated quantitative loading.

Synthesis of Representative Compounds of Structure (Ia')

Reactions were carried out in plastic disposable syringes of the appropriate size, each fitted with a polypropylene frit to retain the resin. After each step, resin batches were washed with DMF (3×) and DCM (3×). Typically, a 0.03 mmol sample of resin 27 (e.g., 50 mg of polystyrene resin with loading of 0.6 mmol Br/g), pre-swollen in DMF, was treated with 1 mL of a 2.0 M solution of amine $R_4$—$NH_2$ (2 mmol) in DMSO at 60° C. for 16–24 hrs.

Next, the resin was reacted with 0.09 mmol of Fmoc amino acid (FmocNH—$CHR_3$—COOH) in the presence of HATU (34 mg, 0.09 mmol) and DIEA (0.032 ml, 0.18 mmol) in DMF (1 mL) until the chloranil test was negative (typically 1–2 h). Subsequently, the Fmoc protection was removed by treatment with a 25% (v/v) piperidine/DMF solution (2 mL) over 20 min.

The resin was then reacted with 0.09 mmol of an Fmoc beta-amino acid (FmocNH—$CHR_5$—$CHR_2$—COOH) in the presence of DIC (0.014 ml, 0.09 mmol) and HOBt (14 mg, 0.09 mmol) in DMF (1 mL) until the Kaiser test was negative (typically 1 hour). The resin was again treated with 25% (v/v) piperidine/DMF solution (2 mL) over 20 min.

Finally, the resin-bound sequence was terminated by reaction with sulfonyl chloride ($R_1SO_2Cl$, 0.3 mmol) in the presence of DIEA (0.106 mL, 0.6 mmol) in DCM (1 mL) for 1 hr (Kaiser test negative). Alternatively, chloroformate $R_1OCOCl$ or isocyanate $R_1NCO$ (the latter does not require presence of DIEA) was used instead of sulfonyl chloride for introduction of the $R_1$ moiety.

The washed and dried resin was re-swollen in DCM, drained and treated with 1 mL of formic acid (96%) overnight at rt. In a number of cases, an elevated temperature up to 60° C. or an extended reaction time was necessary to complete the cyclization (for conditions see Table 2 below). The supernatant was collected and combined with washes (2×0.5 mL of formic acid). The residue obtained after evaporation of formic acid was redissolved in acetonitrile/water 50:50 mixture, frozen and lyophilized.

Table 6 presents representative compounds of this invention synthesized by the above procedure.

TABLE 6
Representative Reverse-Turn Mimetics
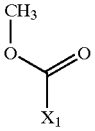
| No. | $R_1$ | $R_2$ | $R_3$ |
|---|---|---|---|
| 28 | 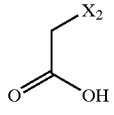 | 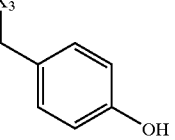 | 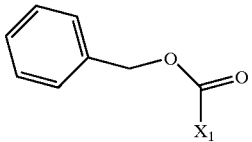 |
| 29 | 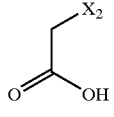 | 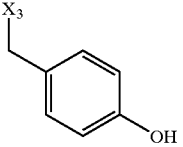 | 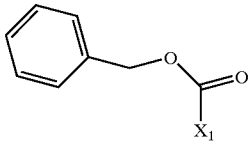 |
| 30 | 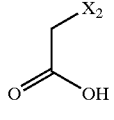 | 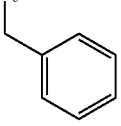 | 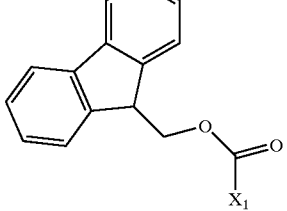 |
| 31 | 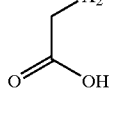 | 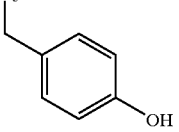 | 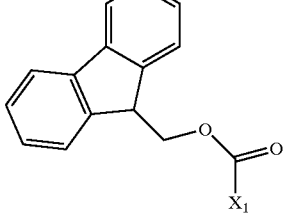 |
| 32 | 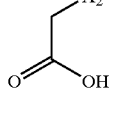 | 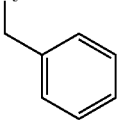 | 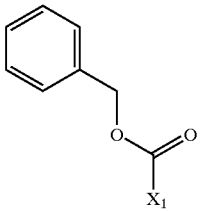 |
| 33 | 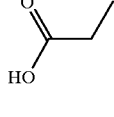 | 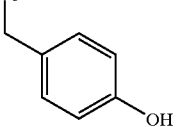 | |

TABLE 6-continued
Representative Reverse-Turn Mimetics
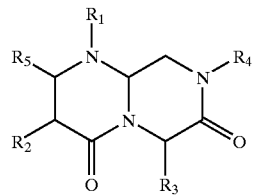
| | | | |
|---|---|---|---|
| 34 | 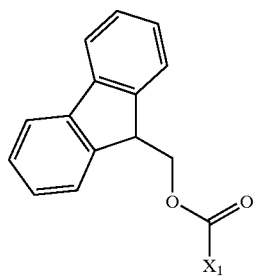 | 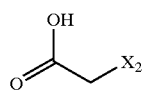 | 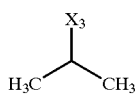 |
| 35 | 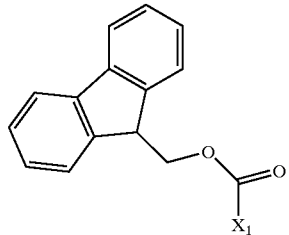 | | 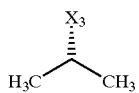 |
| 36 | 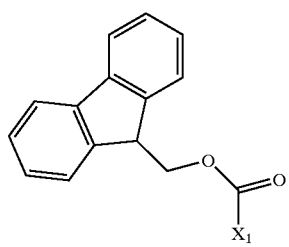 | | 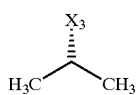 |
| 37 | 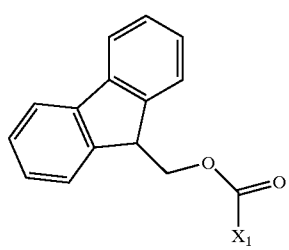 | | 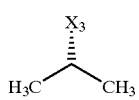 |
| 38 | 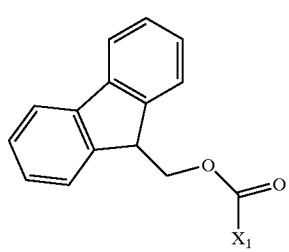 | | 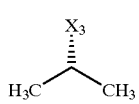 |

TABLE 6-continued

Representative Reverse-Turn Mimetics

| No. | R₄ | R₅ | (M + H⁺) |
|---|---|---|---|
| 39 | naphthalene-2-sulfonyl (X₁) | isopropyl (X₃) | |
| 40 | benzyloxycarbonyl (X₁) | isopropyl (X₃) | |
| 28 | X₄–CH₃ | | 406.3 |
| 29 | X₄–CH₂CH₂–OH | | 512.3 |
| 30 | X₄–CH₂CH₂–OH | | 602.4 |
| 31 | X₄–CH₂CH₂–OH | | 496.3 |
| 32 | X₄–CH₂CH₂–OH | | 600.3 |
| 33 | X₄–CH₂–(4-methoxyphenyl) | | 584.3 |
| 34 | X₄–CH₂CH₂–OH | | 536.4 |
| 35 | X₄–CH₂-(2-pyridyl) | HOOC–CH₂–X₅ | 583.6 |

TABLE 6-continued

Representative Reverse-Turn Mimetics

| # | (structure left) | (structure right) | MW |
|---|---|---|---|
| 36 | 3-pyridyl-CH₂CH₂–X₄ | HO-C(=O)-CH(···X₅)- | 597.6 |
| 37 | 2-pyridyl-CH₂–X₄ | HO-C(=O)-CH(···X₅)- | 569.4 |
| 38 | 4-pyridyl-CH₂–X₄ | HO-C(=O)-CH(···X₅)- | 583.4 |
| 39 | 2-pyridyl-CH₂–X₄ | HO-C(=O)-CH(~X₅)- | 550.5 |
| 40 | 2-pyridyl-CH₂–X₄ | HO-C(=O)-CH(···X₅)- | 495.3 |

Example 12

Activity of Representative Reverse-Turn Mimetics in a Cell Adhesion Assay

An assay measuring the ability of the compounds of Example 1 to antagonize binding of CS1 peptide to $\alpha_4\beta_1$ integrin was performed. A modification of the procedure of Vanderslice, P. et al. (*J. Immunol.*, 1997, 1710–1718) (incorporated herein by reference) was utilized.

In brief, 100 µL/well of a solution of biotinylated CS1 peptide (1 mg/100 mL of phosphate buffered saline (PBS)) was incubated in a NeutrAvidin plate (Pierce) for 1 h at room temperature. The plate was then washed 3× with distilled water and treated with 200 µL of blocking buffer (3% BSA in PBS) for at least 4 h. Blocked plates were washed as above. Harvested Ramos cells ($10^7$/mL) were resuspended in PBS containing 10 µL of calcein AM/mL and incubated 30 min in the dark. This suspension was diluted with 45 mL PBS and the cells harvested by centrifugation and aspiration. The cells were resuspended in binding buffer (~5×$10^5$/mL). If cell lysis was to be monitored ethidium homodimer was added to the buffer to a final concentration of 5 µM. A solution (10 µL) of compound to be tested or control peptide was added to appropriate wells followed by 90 µL of the cell suspension. The plate was incubated at 37° C. for 1 h. When ethidium homodimer was added, fluorescence at 535/617 was measured before rinsing. Otherwise, the plate was washed 3×, 50 µL of lysis buffer was added to each well, the plate rocked in the dark for 10 min, and the fluorescence monitored at 485 nm excitation and 535 nm emission.

Compounds prepared in Example 11 displayed activity in this assay. As such, the compounds of this invention effectively inhibit cell adhesion and possess activity as anti-inflammatory agents.

It will be appreciated that, although specific embodiments of the invention have been described herein for the purposes of illustration, various modifications may be made without departing from the spirit and scope of the invention. Accordingly, the invention is not limited except by the appended claims.

What is claimed is:

1. A compound having the structure:

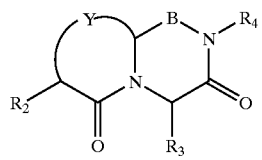

wherein

Y is selected from -A-N(R$_1$)—CH(R')—, -A-N(R$_1$)—C(=O)—, -A-C(=O)—N(R$_1$)—, -A-CH(R$_1$)—O— and -A-CH(R$_1$)—N(R')—;

A is —(CHR')$_n$—, where n=0, 1 or 2;

B is —(CHR'')$_m$—, where m=1, 2 or 3;

R', R'', R$_2$, R$_3$ and R$_5$ are the same or different and independently selected from an amino acid side chain moiety or derivative thereof, a linker and a solid support; and R$_1$ and R$_4$ represent the remainder of the compound; and wherein any two adjacent CH groups or adjacent NH and CH groups on the fused bicyclic ring may optionally form a double bond.

2. The compound of claim 1 wherein Y is -A-N(R$_1$)—CH(R')— and the compound has the structure:

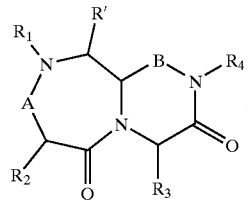

3. The compound of claim 2 wherein two adjacent CH groups on the fused bicyclic ring form a double bond and the compound has the structure:

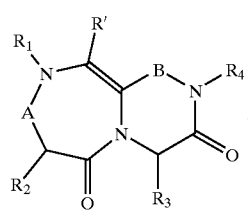

4. The compound of claim 3 wherein A is —(CH$_2$)$_n$—, B is —(CH$_2$)$_m$—, R' is hydrogen and the compound has the structure:

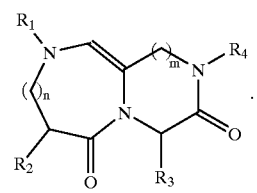

5. The compound of claim 1 wherein Y is -A-N(R$_1$)—C(=O)— and the compound has the structure:

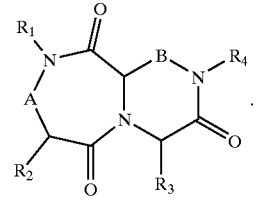

6. The compound of claim 5 wherein A is —(CH$_2$)$_n$—, B is —(CH$_2$)$_m$— and the compound has the structure:

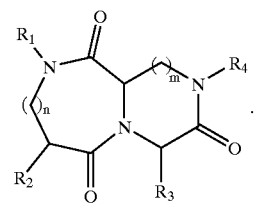

7. The compound of claim 1 wherein Y is -A-C(=O)—N(R$_1$)— and the compound has the structure:

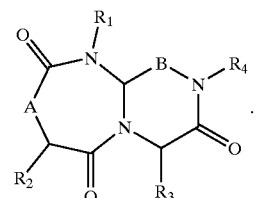

8. The compound of claim 7 wherein A is —(CH$_2$)$_n$—, B is —(CH$_2$)$_m$— and the compound has the structure:

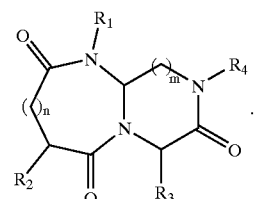

9. The compound of claim 1 wherein Y is -A-CH(R$_1$)—O— and the compound has the structure:

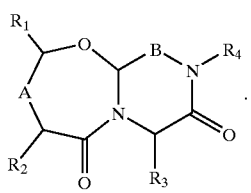

10. The compound of claim 9 wherein A is —(CH$_2$)$_n$—, B is —(CH$_2$)$_m$— compound has the structure:

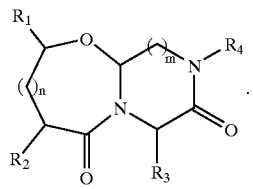

11. The compound of claim 1 wherein Y is -A-CH(R$_1$)—N(R')— and the compound has the structure:

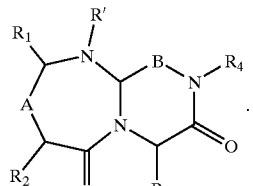

12. The compound of claim 11 wherein two adjacent NH and CH groups on the fused bicyclic ring form a double bond and the compound has the structure:

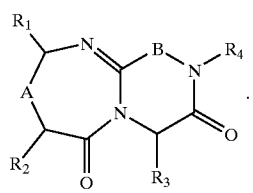

13. The compound of claim 12 wherein A is —(CH$_2$)$_n$—, B is —(CH$_2$)$_m$— and the compound has the structure:

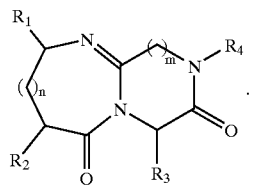

14. A compound having the structure:

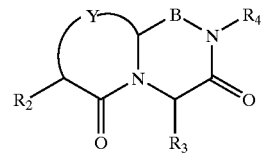

wherein

Y is —CH(R$_5$)-A-N(R$_1$)—;

A is —(CHR')$_n$—, where n=0, 1 or 2;

B is —(CHR'')$_m$—, where m=1, 2 or 3;

R', R'', R$_2$, R$_3$ and R$_5$ are the same or different and independently selected from an amino acid side chain moiety or derivative thereof, a linker and a solid support; and R$_1$ and R$_4$ represent the remainder of the compound; and wherein any two adjacent CH groups or adjacent NH and CH groups on the fused bicyclic ring may optionally form a double bond.

15. The compound of claim 14 wherein A is —(CH$_2$)$_n$—, B is —(CH$_2$)$_m$— and the compound has the structure:

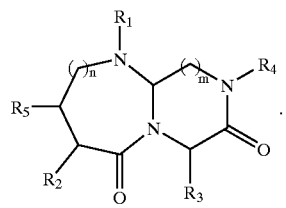

16. The compound of claim 15 wherein n is 0, m is 1 and the compound has the structure:

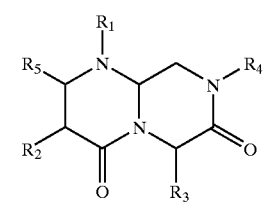

17. A composition comprising a compound of claim 1 or claim 14 in combination with a pharmaceutically acceptable carrier or diluent.

18. A library of compounds, comprising at least one compound of claim 1 or claim 14.

19. A method of identifying a biologically active compound, comprising contacting the library of claim 18 with a target to detect or screen the biologically active compound.

* * * * *

UNITED STATES PATENT AND TRADEMARK OFFICE
CERTIFICATE OF CORRECTION

PATENT NO.  : 6,413,963 B2
DATED       : July 2, 2002
INVENTOR(S) : Michael Kahn et al.

It is certified that error appears in the above-identified patent and that said Letters Patent is hereby corrected as shown below:

Column 49,
Line 12, "wherein A is $–(CH_2)_n-$, B is $–(CH_2)_m-$ compound has the structure" should read -- wherein A is $–(CH_2)_n-$, B is $–(CH_2)_m-$ and the compound has the structure --.

Signed and Sealed this

Fourteenth Day of January, 2003

JAMES E. ROGAN
*Director of the United States Patent and Trademark Office*